United States Patent [19]

Flynn et al.

[11] Patent Number: 5,389,628
[45] Date of Patent: Feb. 14, 1995

[54] AMINO AND NITRO CONTAINING TRICYCLIC COMPOUNDS USEFUL AS INHIBITORS OF ACE

[75] Inventors: Gary A. Flynn; Douglas W. Beight, both of Cincinnati, Ohio

[73] Assignee: Merrell Dow Pharmaceuticals Inc., Cincinnati, Ohio

[21] Appl. No.: 164,047

[22] Filed: Dec. 8, 1993

Related U.S. Application Data

[60] Division of Ser. No. 46,326, Apr. 12, 1993, Pat. No. 5,308,841, which is a division of Ser. No. 979,029, Nov. 20, 1992, abandoned, which is a division of Ser. No. 905,494, Jun. 25, 1992, Pat. No. 5,208,230, which is a continuation of Ser. No. 777,625, Oct. 23, 1991, abandoned, which is a continuation-in-part of Ser. No. 633,572, Dec. 21, 1990, abandoned.

[51] Int. Cl.$^6$ ............... C07D 498/04; C07D 487/04; C07D 513/04; A61K 31/55
[52] U.S. Cl. ............................. 514/215; 540/521
[58] Field of Search ................ 540/521; 514/215

[56] References Cited

U.S. PATENT DOCUMENTS

| | | | |
|---|---|---|---|
| 3,334,091 | 7/1967 | Houlihan | 260/243 |
| 3,334,095 | 8/1967 | Houlihan | 260/244 |
| 4,080,449 | 3/1978 | Croisier et al. | 424/244 |
| 4,320,057 | 3/1982 | Freed et al. | 544/47 |
| 4,391,752 | 7/1983 | Crossley | 548/540 |
| 4,399,136 | 8/1983 | Hassall et al. | 544/235 |
| 4,487,929 | 12/1984 | Hassall et al. | 544/224 |
| 4,692,438 | 9/1987 | Hassall et al. | 514/183 |
| 4,716,232 | 12/1987 | Ternansky | 548/112 |
| 4,734,364 | 3/1988 | Holmes | 548/364 |
| 4,734,505 | 3/1988 | Holmes | 548/364 |
| 4,762,924 | 8/1988 | Hassall et al. | 540/501 |
| 4,782,149 | 11/1988 | Lawton et al. | 540/500 |
| 4,785,093 | 11/1988 | Hassall et al. | 540/460 |
| 4,826,980 | 5/1989 | Hassall et al. | 544/224 |
| 5,208,230 | 5/1993 | Flynn et al. | 540/521 |

FOREIGN PATENT DOCUMENTS 0128728 12/1984 European Pat. Off. .
0322914 12/1988 European Pat. Off. .
0492369 7/1992 European Pat. Off. .
9302099 2/1993 WIPO .

OTHER PUBLICATIONS

Flynn et al., *J. Med. Chem.* 1993, 36 2420–2423.
J. Timothy D. Ocain et al., *Med. Chem.* 1992, 35, 823–832.
*Bioorganic and Medical Chem Letters*, vol. 1, 309, 1991.
Fournie-Zaluski, Marie-Claude et al., *J. Med. Chem.*, 1992 vol. 35, pp. 2473–2481.
Forunie-Zaluski, Marie-Claude et al., *J. Med. Chem.*, 1992 vol. 35, pp. 1259–1266.
French, John F., *Jour. of Pharm and Exper. Therapeutics*, vol. 268, No. 1, pp. 180–186 (1994).
W. H. Parsons et al. *Biochemical and Biophysical Research Communications* vol. 117, No. 1, 1993 (Nov. 30, 1983).
Burkholder, et al. *Bioorganic and Medical Chem. Letters*, vol. 3, No. 2, pp. 231–234, 1993.

Primary Examiner—Mark L. Berch
Attorney, Agent, or Firm—Charlotte L. Barney

[57] ABSTRACT

The present invention relates to compounds of the formula

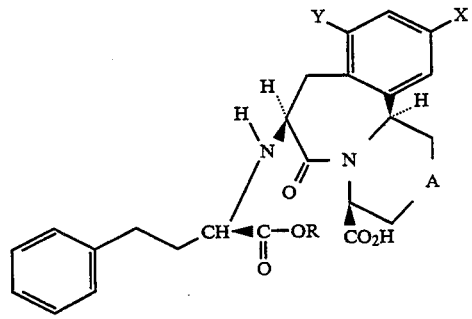

wherein
A is methylene, oxygen, sulfur or N—B wherein B is $R_1$ or $COR_2$ wherein $R_1$ is hydrogen, a $C_1$–$C_4$ alkyl or an Ar—Z— group wherein Ar is aryl and Z is a (Abstract continued on next page.)

$C_0$–$C_4$ alkyl and $R_2$ is a —$CF_3$, a $C_1$–$C_{10}$ alkyl or an Ar—Z group;

R is hydrogen or a $C_1$–$C_4$ alkyl; and

X and Y are each independently hydrogen, nitro or amino, with the proviso that when X is nitro or amino, Y must be hydrogen, and when Y is nitro or amino, X must be hydrogen; and pharmaceutically acceptable salts thereof, which are inhibitors of Angiotensin Converting Enzyme.

10 Claims, No Drawings

AMINO AND NITRO CONTAINING TRICYCLIC COMPOUNDS USEFUL AS INHIBITORS OF ACE

This is a division, of application Ser. No. 08/046,326, filed Apr. 12, 1993, U.S. Pat. No. 5,308,841, which is a divisional of application Ser. No. 07/979,029, filed Nov. 20, 1992, now abandoned, which is a divisional of application Ser. No. 07/905,494, filed Jun. 25, 1992, now U.S. Pat. No. 5,208,230, issued May 4, 1993, which is a continuation of application Ser. No. 07/777,625, filed Oct. 23, 1991, now abandoned, which is a continuation-in-part of application Ser. No. 07/633,572, filed Dec. 21, 1990, now abandoned.

BACKGROUND OF THE INVENTION

The compounds of the present invention are inhibitors of Angiotensin-Converting Enzyme (ACE). ACE is a peptidyl dipeptidase which catalyzes the conversion of angiotensin I to angiotensin II. Angiotensin II is a powerful vasopressor which also stimulates aldosterone secretion by the adrenal cortex.

Inhibition of ACE lowers levels of angiotensin II and thus inhibits the vasopressor, hypertensive and hyperaldosteronemic effects caused thereby. It is known that inhibition of ACE is useful in the treatment of patients suffering from disease states such as hypertension and chronic congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652–3, MacMillan Publishing Co., New York, N.Y.]. In addition, it has been disclosed that ACE inhibitors are useful in treating cognitive disorders [German Application No. 3901-291-A, published Aug. 3, 1989].

Certain tricyclic compounds such as that described by Flynn et al. [J. Amer. Chem. Soc. 109, 7914–15 (1987)] and Flynn and Beight [European Patent Application Publication No. 0 249 223 A2, published Dec. 16, 1987] are known as ACE inhibitors. The compounds of the present invention differ from these tricyclic inhibitors of ACE by having an amino or nitro substituent on the aromatic moiety of the tricyclic structure.

It has now been found that the amino or nitro substituted compounds of the present invention possess an unexpectedly prolonged duration of activity in comparison to other ACE inhibitors of similar structure.

SUMMARY OF THE INVENTION

The present invention provides novel compounds of the formula (1)

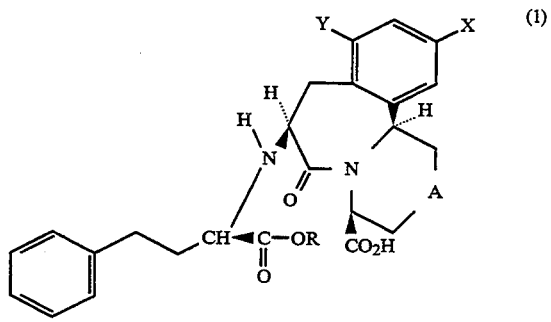

wherein

A is methylene, oxygen, sulfur or N—B wherein B is $R_1$ or $COR_2$ wherein $R_1$ is hydrogen, a $C_1$–$C_4$ alkyl or an Ar—Z— group wherein Ar is aryl and Z is a $C_0$–$C_4$ alkyl and $R_2$ is a —$CF_3$, a $C_1$–$C_{10}$ alkyl or an Ar—Z group;

R is hydrogen or a $C_1$–$C_4$ alkyl; and

X and Y are each independently hydrogen, nitro or amino, with the proviso that one of X and Y is hydrogen and one of X and Y is other than hydrogen; and the pharmaceutically acceptable salts thereof.

The present invention further provides a method of inhibiting ACE in a patient in need thereof comprising administering to said patient an effective ACE inhibitory amount of a compound of formula (1).

In addition, the present invention provides a composition comprising an assayable amount of a compound of formula (1) in admixture or otherwise in association with an inert carrier. The present invention also provides a pharmaceutical composition comprising an effective immunosuppressive amount of a compound of formula (1) in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "$C_1$–$C_{10}$ alkyl" refers to a saturated straight or branched chain hydrocarbyl radical of one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. The term "halogen", "halo", "halide" or "X" refers to a chlorine, bromine, or iodine atom.

As used herein, the term "Ar—Z—" refers to a radical wherein Ar is an aryl group and Z is a $C_0$–$C_4$ alkyl. The term "Ar" refers to a phenyl or naphthyl group unsubstituted or substituted with from one to three substituents selected from the group consisting of methylenedioxy, hydroxy, $C_0$–$C_4$ alkoxy, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Z—" are phenyl, naphthyl, phenylmethyl or benzyl, phenylethyl, p-methoxybenzyl, p-fluorobenzyl and p-chlorobenzyl.

The compounds of formula (1), wherein R is hydrogen can be prepared by utilizing procedures and techniques well known and appreciated by one of ordinary skill in the art. A general synthetic scheme for preparing these compounds is set forth in Scheme A wherein all substituents, unless otherwise indicated, are previously defined.

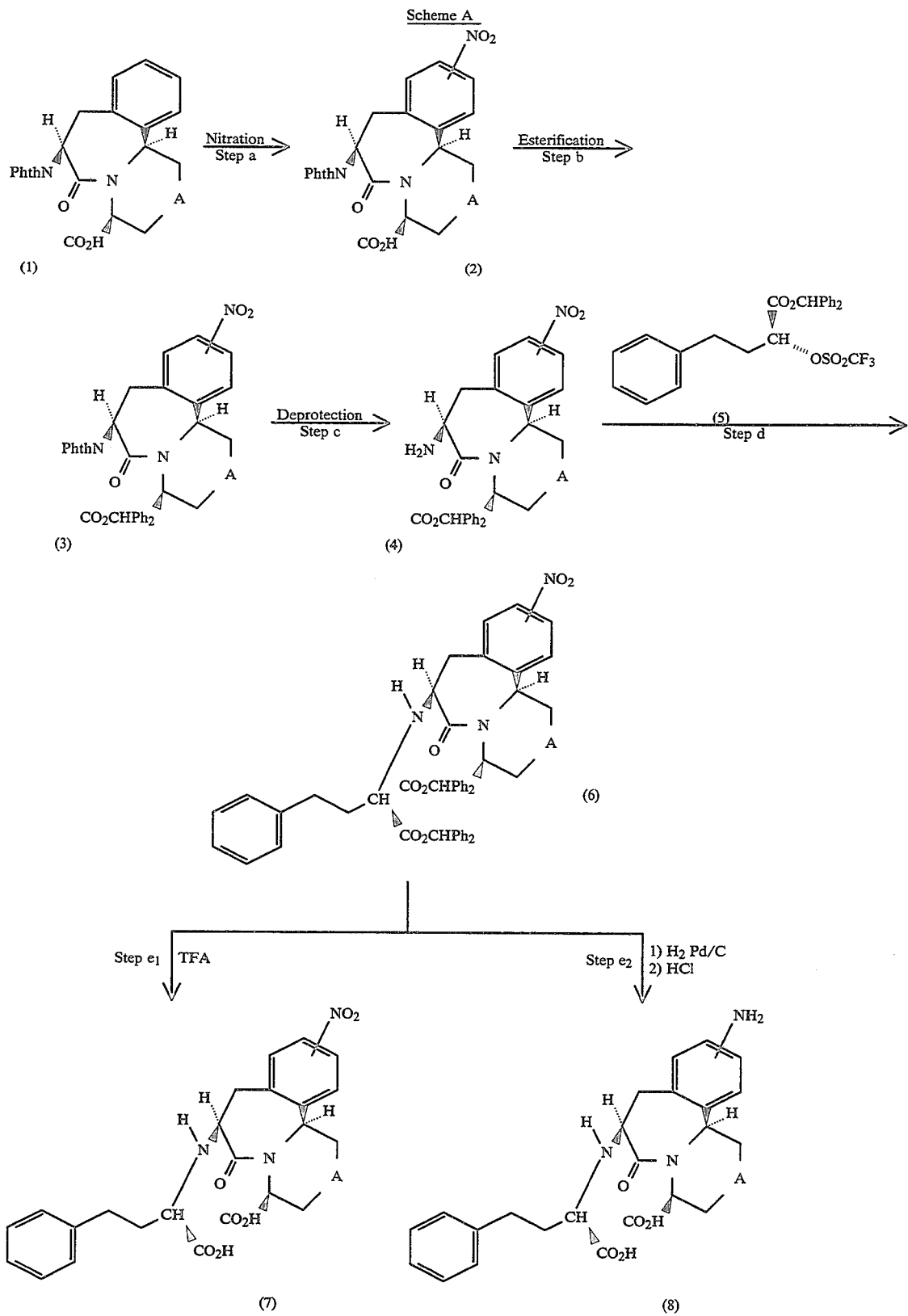
Scheme A provides a general synthetic scheme for preparing compounds of formula (1) wherein R is hydrogen.
In step a, the appropriate phthalimide protected amino/carboxylic acid compound of structure (1) is nitrated to give a mixture of the corresponding 9-nitro and 11-nitro/phthalimide protected amino/carboxylic acid compounds of structure (2).

For example, the appropriate phthalimide protected amino/carboxylic acid compound of structure (1) is contacted with a molar excess of a nitrating agent, such as nitronium tetrafluoroborate. The reactants are typically contacted in a suitable organic solvent, such as methylene chloride. The reactants are typically stirred together for a period of time ranging from 10–50 hours and at a temperature range of from −60° C. to 10° C. The 9-nitro and 11-nitro/phthalimide protected amino/carboxylic acid compounds of structure (2) is recovered from the reaction mixture by extractive methods as is known in the art. They can be separated by silica gel chromatography.

In step b, the appropriate individual 9-nitro and 11-nitro/phthalimide protected amino/carboxylic acid compounds of structure (2) is esterified to give the corresponding individual 9-nitro and 11-nitro/phthalimide protected amino/carboxylic acid, diphenylmethyl ester compounds of structure (3).

For example, the appropriate individual 9-nitro and 11-nitro/phthalimide protected amino/carboxylic acid compounds of structure (2) is contacted with a molar equivalent of an appropriate diphenylmethylating agent, such as diphenyldiazomethane. The reactants are typically contacted in a suitable organic solvent, such as methylene chloride. The reactants are typically stirred together at room temperature for a period of time ranging from 1–10 days. The corresponding individual 9-nitro and 11-nitro/phthalimide protected amino/carboxylic acid, diphenylmethyl ester compounds of structure (3) is recovered from the reaction zone by evaporation of the solvent. They may be purified by silica gel chromatography.

In step c, the phthalimide protecting group of the appropriate individual 9-nitro and 11-nitro/phthalimide protected amino/carboxylic acid, diphenylmethyl ester compounds of structure (3) is removed to give the corresponding individual 9-nitro and 11-nitro/amino/carboxylic acid, diphenylmethyl ester compounds of structure (4).

For example, the appropriate individual 9-nitro and 11-nitro/phthalimide protected amino/carboxylic acid, diphenylmethyl ester compounds of structure (3) is contacted with a molar excess of hydrazine monohydrate. The reactants are typically contacted in protic organic solvent, such as methanol. The reactants are typically stirred together at room temperature for a period of time ranging from 5–24 hours. The corresponding individual 9-nitro and 11-nitro/amino/carboxylic acid, diphenylmethyl ester compounds structure (4) is recovered from the reaction zone by evaporation of the solvent, redissolving in $CHCl_3$, filtration to remove phthal-hydrazide and removal of the $CHCl_3$ in vacuo.

In step d, the amino functionality of the appropriate individual 9-nitro and 11-nitro/amino/carboxylic acid, diphenylmethyl ester compound s of structure (4) is alkylated with (R)-2-trifluoromethanesulfonyl-4-phenylbutyric acid, diphenylmethyl ester (5) to give the corresponding individual 9-nitro and 11-nitro/[1-(carbodiphenylmethoxy)-3-phenyl]propylamino/carboxylic acid compounds, diphenylmethyl ester compounds of structure (6).

For example, the appropriate individual 9-nitro and 11-nitro/amino/carboxylic acid, diphenylmethyl ester compounds of structure (4) is contacted with a molar excess of (R)-trifluoromethanesulfonyl-4-phenylbutyric acid, diphenylmetheyl ester (5) and a molar excess of strong, non-nucleophilic base, such as Proton Sponge. The reactants are typically contacted in a suitable organic solvent such as methylene chloride. The reactants are typically stirred together at room temperature for a period of time ranging from 10–30 hours. The corresponding individual 9-nitro and 11-nitro/[1-(carbodiphenylmethoxy)-3-phenyl]propylamino/carboxylic acid, diphenylmethyl ester compounds of structure (6) is recovered from the reaction zone by silica gel chromatography.

In step $e_1$, the diphenylmethyl ester functionalities of the appropriate individual 9-nitro and 11-nitro/[1-(carbodiphenylmethoxy)-3-phenyl]propylamino/carboxylic acid, diphenylmethyl ester compounds of structure (6) is hydrolyzed to give the corresponding individual 9-nitro and 11-nitro/[1-(carboxy)-3-phenyl]propylamino/carboxylic acid compounds of structure (7).

For example, the appropriate individual 9-nitro and 11-nitro/[1-(carbodiphenylmethoxy)-3-phenyl]propylamino/carboxylic acid, diphenylmethyl ester compounds of structure (6) is contacted with a molar excess of an acid, such as trifluoroacetic acid. The reactants are typically contacted in a suitable organic solvent such as methylene chloride. The reactants are typically stirred together at room temperature for a period of time ranging from 1-24 hours. The corresponding individual 9-nitro and 11-nitro/[1-(carboxy)-3-phenyl]propylamino/carboxylic acid compounds of structure (7) is recovered from the reaction zone by removal of solvent and trituration to remove nonpolar by-products followed by reverse phase HPLC where required.

In step $e_2$, the nitro functionality of the appropriate individual 9-nitro and 11-nitro/[1-(carboxy)-3-phenyl]propylamino/carboxylic acid, diphenylmethyl ester compounds of structure (6) is reduced concurrently with diphenylmethyl ester hydrogenolysis to give the corresponding individual 9-amino and 11-amino/[1-(carboxy)-3-phenyl]propylamino/carboxylic acid compounds of structure (8).

For example, the individual 9-nitro and 11-nitro/[1-(carboxy)-3-phenyl]propylamino/carboxylic acid, diphenylmethyl ester compounds of structure (6) is contacted with a catalytic amount of a hydrogenation catalyst, such as 10% palladium/carbon. The reactants are typically contacted in a suitable solvent mixture such as tetrahydrofuran/water. The reactants are typically shaken under a hydrogen atmosphere of 35-45 psi at room temperature for a period of time ranging from 5-24 hours. The individual 9-amino and 11-amino/[1-(carboxy)-3-phenyl]propylamino/carboxylic acid compounds of structure (8) is recovered from the reaction zone by evaporation of the solvent. They may then be converted to their dihydrochloride salts and triturated with hexane to remove the diphenylmethane.

For those compounds of formula (1) wherein A is N—$COR_2$, the N—$COR_2$ group of the appropriate individual 9-nitro and 11-nitro/[1-(carboxy)-3-phenyl]propylamino/carboxylic acid compounds of structure (7) or the appropriate individual 9-amino and 11-amino/[1-(carboxy)-3-phenyl]propylamino/carboxylic acid compounds of structure (8) may be cleaved by techniques and procedures well known an appreciated in the art, such as lithium hydroxide, to give the corresponding compounds of formula (1) wherein A is NH.

The compounds of formula (1), wherein R is a $C_1$–$C_4$ alkyl can be prepared by utilizing procedures and techniques well known and appreciated by one of ordinary skill in the art. A general synthetic scheme for preparing these compounds is set forth in Scheme B wherein all substituents, unless otherwise indicated, are previously defined.

phenylmethyl ester compounds of structure (10) as described previously in Scheme A, step d.

In step b₁, the carboxylic acid, diphenylmethyl ester functionality of the appropriate individual 9-nitro and 11-nitro/[1-(carboalkoxy)-3-phenyl]propylamino/car-

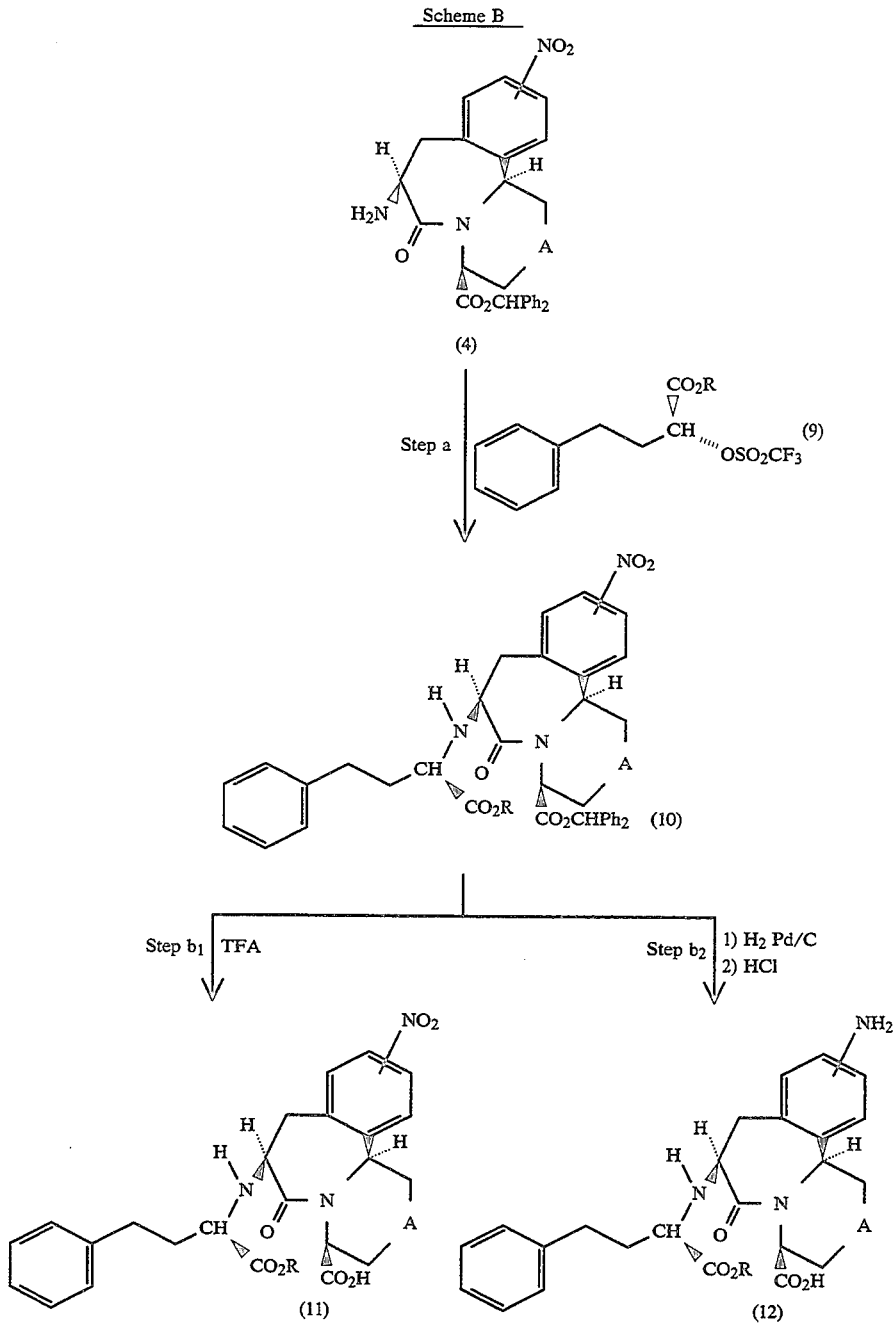

Scheme B provides a general synthetic scheme for preparing compounds of formula (1) wherein R is $C_1$–$C_4$ alkyl.

In step a, the amino functionality of the appropriate individual 9-nitro and 11-nitro/amino/carboxylic acid, diphenylmethyl ester compounds of structure (4) is alkylated with (R)-2-trifluoromethanesulfonyl-4-phenylbutyric acid, $C_1$–$C_4$ alkyl ester (9) to give the corresponding individual 9-nitro and 11-nitro/[1-(carboalkoxy)-3-phenyl]propylamino/carboxylic acid, diboxylic acid, diphenylmethyl ester compounds of structure (10) is hydrolyzed to give the corresponding individual 9-nitro and 11-nitro/[1-(carboalkoxy)-3-phenyl]-propylamino/carboxylic acid compounds of structure (11) as described previously in Scheme A, step e₁.

In step b₂, the nitro functionality of the appropriate individual 9-nitro and 11-nitro/[1-(carboalkoxy)-3-phenyl]propylamino/carboxylic acid, diphenylmethyl ester compounds of structure (10) is reduced concurrently with diphenylmethyl ester hydrogenolysis to give the corresponding individual 9-amino and 11- amino/[1-(carboalkoxy)-3-phenyl]propylamino/carboxylic acid compounds structure (12) as described previously in Scheme A, step e₂.

For those compounds of formula (1) wherein A is N—COR₂, the N—COR₂ group of the appropriate individual 9-nitro and 11-nitro/[1-(carboalkoxy)-3-phenyl]propylamino/carboxylic acid compounds of structure (11) or the appropriate 9-amino and 11-amino/[1-(carboalkoxy)-3-phenyl]propylamino/carboxylic acid compounds structure (12) may be cleaved by techniques and procedures well known an appreciated in the art, such as lithium hydroxide, to give the corresponding compounds of formula (1) wherein A is NH.

Phthalimide protected amino/carboxylic acid compounds of structure 1 wherein A is 0 may be prepared as described in Scheme C. In Scheme C, all substituents unless otherwise indicated are as previously defined.

Scheme C

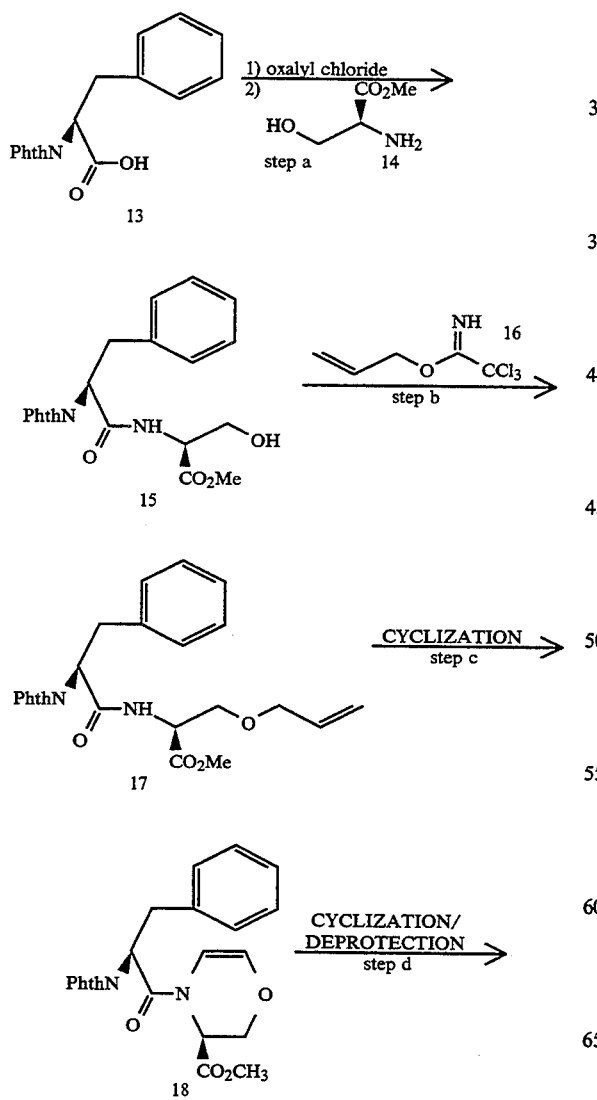

-continued
Scheme C

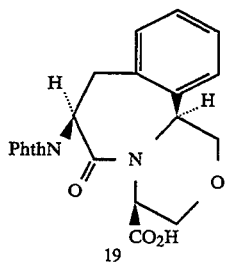

Scheme C provides a general synthetic procedure for preparing phthalimide protected amino/carboxylic acid compounds of structure 1 wherein A is 0.

In step a, the appropriate phthalimide blocked (S)-phenylalanine derivative of structure (13) is converted to the corresponding acid chloride, then reacted with the appropriate L-serine methyl ester of structure (14) to give the corresponding 1-oxo-3-phenylpropyl-L-serine methyl ester of structure (15).

For example, the appropriate phthalimide blocked (S)-phenylalanine derivative of structure (13) can be reacted with oxalyl chloride in a suitable aprotic solvent, such as methylene chloride. The resulting acid chloride can then be coupled with the appropriate L-serine methyl ester of structure (14) using N-methylmorpholine in a suitable aprotic solvent, such as dimethylformamide, to give the appropriate 1-oxo-3-phenylpropyl-L-serine methyl ester of structure (15).

In step b, the hydroxy functionality of the appropriate 1-oxo-3-phenylpropyl-L-serine methyl ester of structure (15) is allylated with the allyl imidate of structure (16) to give the corresponding 1-oxo-3-phenylpropyl-L-serine-O-allyl methyl ester of structure (17).

For example, the appropriate 1-oxo-3-phenylpropyl-L-serine methyl ester of structure (15) is contacted with 2 molar equivalents of the allyl imidate of structure (16) and a molar equivalent of a suitable acid such as trifluoromethanesulfonic acid. The reactants are typically contacted in a suitable organic solvent mixture such as methylene chloride/cyclohexane. The reactants are typically stirred together at room temperature under an inert atmosphere for a period of time ranging from 2–24 hours. The 1-oxo-3-phenylpropyl-L-serine-O-allyl methyl ester of structure (17) is recovered from the reaction zone by extractive methods as is known in the art. It may be purified by silica gel chromatography or crystalization.

In step c, the appropriate 1-oxo-3-phenylpropyl-L-serine-O-allyl methyl ester of structure (17) is cyclized to give the corresponding (4S)-enamine of structure (18).

For example, the appropriate 1-oxo-3-phenylpropyl-L-serine-O-allyl methyl ester of structure (17) is first contacted with a molar excess of a mixture of ozone/oxygen. The reactants are typically contacted in a suitable organic solvent mixture such as methylene chloride/methanol. The reactants are typically stirred together for a period of time ranging from 5 minutes to 30 minutes or until a blue color persists and at a temperature range of from −78° C. to −40° C. The reaction is quenched with an excess of methylsulfide and the intermediate aldehyde compound recovered from the reaction zone by extractive methods as is known in the art.

The intermediate aldehyde compound is then contacted with trifluoroacetic acid in a suitable aprotic solvent, such as methylene chloride to give the corresponding (4S)-enamine of structure (18).

In step d, the appropriate (4S)-enamine of structure (18) is cyclized and the methyl ester functionality is removed to give the corresponding phthalimide protected amino/carboxylic acid compound of structure (19) by an acid catalyzed Friedel-Crafts reaction. For example, the appropriate (4S)-enamine of structure (18) can be converted to the corresponding phthalimide protected amino/carboxylic acid compound of structure (19) by treatment with a mixture of trifluoromethane sulfonic acid and trifluoroacetic anhydride in a suitable aprotic solvent, such as methylene chloride.

Phthalimide protected amino/carboxylic acid compounds of structure 1 wherein A is N—B may be prepared as described in Scheme D. In Scheme D, all substituents unless otherwise indicated are as previously defined.

Scheme D

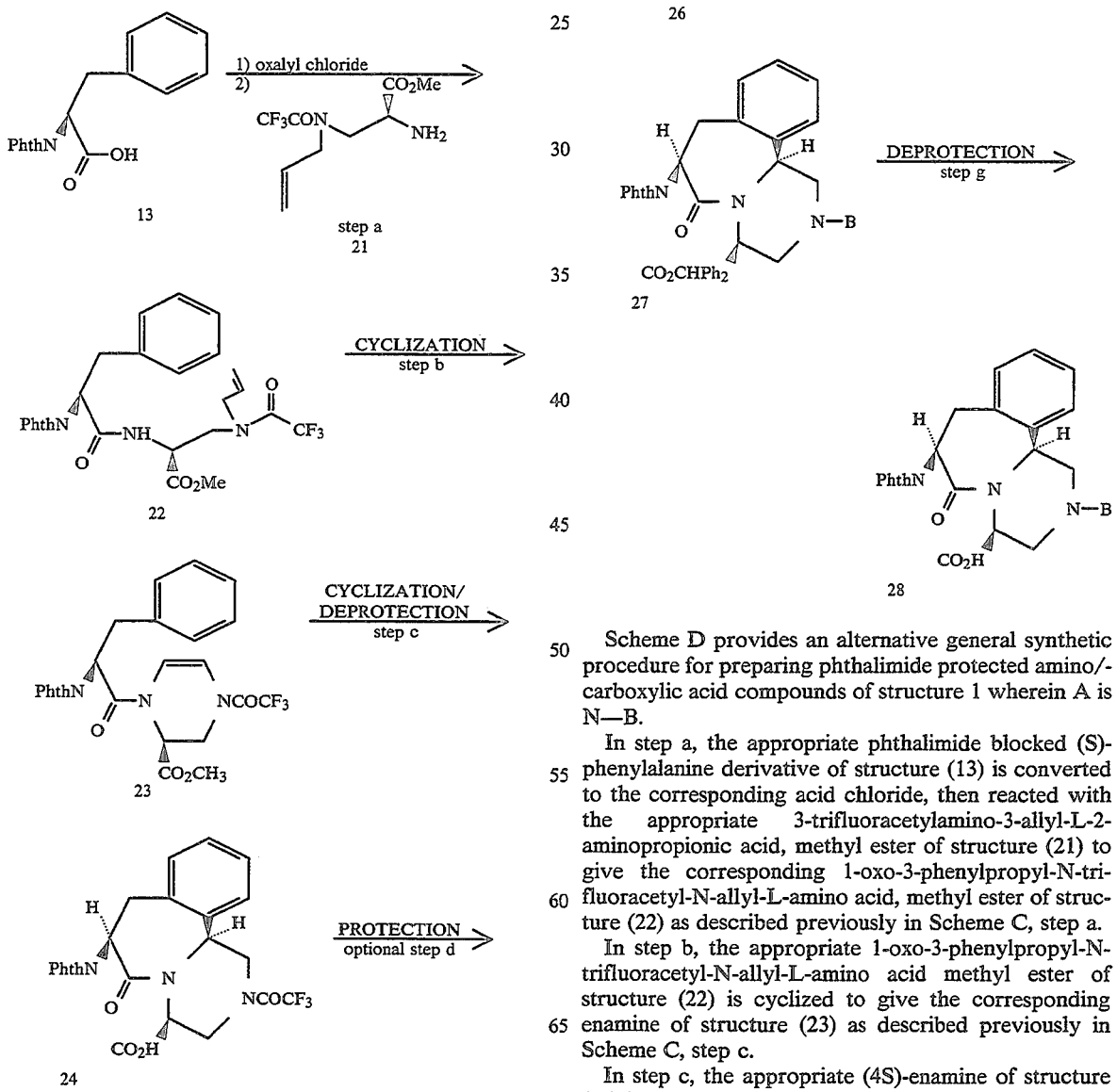

Scheme D provides an alternative general synthetic procedure for preparing phthalimide protected amino/carboxylic acid compounds of structure 1 wherein A is N—B.

In step a, the appropriate phthalimide blocked (S)-phenylalanine derivative of structure (13) is converted to the corresponding acid chloride, then reacted with the appropriate 3-trifluoracetylamino-3-allyl-L-2-aminopropionic acid, methyl ester of structure (21) to give the corresponding 1-oxo-3-phenylpropyl-N-trifluoracetyl-N-allyl-L-amino acid, methyl ester of structure (22) as described previously in Scheme C, step a.

In step b, the appropriate 1-oxo-3-phenylpropyl-N-trifluoracetyl-N-allyl-L-amino acid methyl ester of structure (22) is cyclized to give the corresponding enamine of structure (23) as described previously in Scheme C, step c.

In step c, the appropriate (4S)-enamine of structure (23) is cyclized to give the corresponding phthalimide protected amino/carboxylic acid compound of structure (24) as described previously in Scheme C, step d.

In optional step d, it is necessary to reesterify the carboxy functionality of the phthalimide protected amino/carboxylic acid compound of structure (24) in order to carry out optional steps e and f. For example, treatment of the crude phthalimide protected amino/carboxylic acid compound of structure (24) with bromodiphenylmethane in a suitable aprotic solvent, such as dimethylformamide along with a non-nucleophilic base, such as cesium carbonate, may be used to give the corresponding phthalimide protected amino/carboxylic acid, diphenylmethyl ester compound of structure (25).

In optional step e, the trifluroacetate protecting group of the appropriate phthalimide protected amino/carboxylic acid, diphenylmethyl ester compound of structure (25) is removed with a base such as lithium hydroxide as is known in the art to give the corresponding phthalimide protected amino/carboxylic acid, diphenylmethyl ester compound of structure (26).

In optional step f, the free amino functionality of the phthalimide protected amino/carboxylic acid, diphenylmethyl ester compound of structure (26) is alkylated or acylated by techniques and procedures known in the art to give the corresponding phthalimide protected amino/carboxylic acid, diphenylmethyl ester compound of structure (27) wherein B is $R_1$ or $COR_2$ which may be used in Scheme A.

In step g, the diphenylmethyl ester functionality of the appropriate phthalimide protected amino/carboxylic acid, diphenylmethyl ester compound of structure (25), the appropriate phthalimide protected amino/carboxylic acid, diphenylmethyl ester compound of structure (26) or the appropriate phthalimide protected amino/carboxylic acid, diphenylmethyl ester compound of structure (27) is removed to give the corresponding phthalimide protected amino/carboxylic acid compound of structure (28) as described previously in Scheme A, step $e_1$.

Starting materials for use in Schemes A through D are readily available to one of ordinary skill in the art. For example, certain tricyclic amino compounds of structure 1 wherein X is S are described in European Patent 0 249 223 (Dec. 16, 1987) and certain other tricyclic amino compounds of structure 1 wherein A is methylene may be prepared as described in European Patent Application of Flynn and Beight, Application #34533A EP (Jun. 11, 1987). Diphenyldiazomethane is described in Org. Syn., Coll. Vol. (III), 351. Certain (R)-2-hydroxy-4-phenylbutyric acid esters are described in U.S. Pat. No. 4,837,354 of Flynn and Beight (Jun. 6, 1989). Ethyl (R)-2-trifluoromethanesulfonyl-4-phenyl-butyrate is described in Tetrahedron Lett. 25, 1143–46 1984.

The following examples present typical syntheses as described in Schemes A through D. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 1

[4S-[4α,7α(R*),12bβ]]-7-[(S-1-Carboxy-3-phenyl-propyl)amino]-1,2,3,4,6,7,8,12b-octahydro-9-nitro-6-oxopyrido[2, 1-a][2 ]benzazepine-4-carboxylic acid Scheme A, Step a: [4S-[4α,7α(R*),12bβ]]-7-[1,3,-Dihydro1,3-dioxo-2H-isoindol-2-yl]-1,2,3,4,6,7,8,12b-octahydro-9-nitro-6-oxopyrido[2,1-a][2]benzazepine-4-carboxylic acid and [4S-[4α,7α(R*),12bβ]]-7-[1,3-dihydro-1,3-dioxo-2H-isoindol-2-yl]-1,2,3,4,6,7,8,12b-octahydro-11-nitro-6-oxopyrido[2,1-a][2]benzazepine-4-carboxylic acid Dissolve [4S-[4α,7α(R*),12bβ]]-7-[1,3-dihydro-1,3-dioxo-2H-isoindol-2-yl]-1,2,3,4,6,7,8,12b-octahydro-6-oxopyrido[2,1-a][2]benzazepine-4-carboxylic acid (1.46 g, 3.5 mmol) in methylene chloride (10 mL) and cool to −60° C. Add, by dropwise addition, a solution of nitronium tetrafluoroborate (25 mL of a 0.5M solution in sulfolane, 12.5 mmol) in methylene chloride (15 mL). Warm slowly to 10° C. over 34 hours. Partition between methylene chloride (75 mL) and water (75 mL). Separate the aqueous phase and extract with methylene chloride (50 mL). Combine the organic phases, dry (MgSO4) and evaporate the solvent in vacuo. Purify and separate by flash silica gel chromatography (1:1 ethyl acetate/hexane→1:1 ethyl acetate/hexane with 5% acetic acid→2:1 ethyl acetate/hexane with 5% acetic acid) to give the 11-nitro title compound (1.01 g, 64.3%) and the 9-nitro title compound (0.43 g, 27.4%) as brown foams.

Scheme A, Step b: [4S-[4α,7α(R*),12bβ]]-7-[1,3-Dihydro-1,3-dioxo-2H-isoindol-2-yl]-1,2,3,4,6,7,8,12b-octahydro-9-nitro-6-oxopyrido[2,1-a][2]benzazepine-4-carboxylic acid, diphenylmethyl ester Dissolve [4S-[4α,7α(R*),12bβ]]-7-[1,3-dihydro-1,3-dioxo-2H-isoindol-2-yl[-1,2,3,4,6,7,8,12b,-octahydro-9-nitro-6-oxopyrido[2,1-a][2]benzazepine-4-carboxylic acid (674 mg, 1.50 mmol) in methylene chloride (1 mL). Add diphenyldiazomethane (291 mg, 1.50 mol) and let stand for several days in which time the methylene chloride evaporates. Purify the residue by silica gel chromatography (40% ethyl acetate/hexane→55% ethyl acetate/hexane) to give the title compound as a white foam (613 mg, 66%).

Anal. Calcd for $C_{36}H_{29}N_3O_7$: C, 70.23; H, 4,75; N, 6.83; Found: C, 70.23; H, 4,77; N, 6.63.

Scheme A, Step c: [4S-[4α,7α(R*),12bβ]]-7-Amino-1,2,3,4,6,7,8,12b-octahydro-9-nitro-6-oxopyrido[2,1-a][2]benzazepine-4-carboxylic acid, diphenylmethyl ester Slurry [4S-[4α,7α(R*),12bβ]]-7-[1,3-dihydro-1,3-dioxo-2H-isoindol-2-yl]-1,2,3,4,6,7,8,12b-octahydro-9-nitro-6-oxopyrido[2,1-a][2]benzazepine-4-carboxylic acid, diphenylmethyl ester (200 mg, 0.324 mmol) in methanol (6 mL) and add hydrazine hydrate (1.0 mL of a 1M solution in methanol, 1.0 mmol). Stir at room temperature under an argon atmosphere for 20 hours. Dilute with methylene chloride (30 mL) and stir for 2 hours. Filter and concentrate in vacuo. Take up the residue in methylene chloride and filter again. Wash the filtrate with water, dry (MgSO4) and evaporate the solvent in vacuo to give the title compound as a yellow foam (165 mg).

Scheme A, Step d: [4S-[4α,7α(R*),12bβ]]-7-[[S-1-[Carbodiphenylmethoxy]-3-phenylpropyl]amino]-1,2,3,4,6,7,8,12b-octahydro-9-nitro-6-oxopyrido[2,1- a][2]benzazepine-4-carboxylic acid, diphenylmethyl ester

Dissolve (R)-2-hydroxy-4-phenylbutyric acid, ethyl ester (4.16 g, 20 mmol) in methanol (40 mL). Add 1N lithium hydroxide (25 mL, 25 mmol) and stir under an atmosphere of argon for 3.5 hours. Acidify with 1N hydrochloric acid (25 mL), saturate with sodium chloride and extract with ethyl acetate (3×25 mL). Combine the organic phases, dry (MgSO$_4$) and evaporate the solvent in vacuo. Take up the residue in methylene chloride (20 mL) and add diphenyldiazomethane (3.36 g, 17.3 mmol). Stir overnight and wash with saturated sodium hydrogen carbonate (2×). Dry (MgSO$_4$), evaporate the solvent in vacuo and recrystallize (methylene chloride/hexane then again with cyclohexane) to give (R)-2-hydroxy-4-phenylbutyric acid, diphenylmethyl ester as white needles (2.3 g, 38%); mp 82°–84° C.

Anal. Calcd for $C_{23}H_{22}O_3$: C, 79.74; H, 6.40; Found: C, 79,76; H, 6.41.

Dissolve (R)-2-hydroxy-4-phenylbutyric acid, diphenylmethyl ester (1.38 g, 4.0 mmol) in methylene chloride (12 mL). Add pyridine (0.32 mL, 4 mmol), place under an argon atmosphere and cool to −10° C. Add, by dropwise addition, a solution of trifluoromethanesulfonic anhydride (0.673 mL, 4.0 mmol) in methylene chloride (2 mL). Stir at −10° to −20° C. for 2 hours, dilute with hexane (10 mL) and filter. Evaporate the solvent in vacuo to give (R)-2-trifluoromethanesulfonyl-4-phenylbutyric acid, diphenylmethyl ester.

Dissolve [4S-[4α, 7α(R*),12bβ]]-7-amino-1,2,3,4,6,7,8,12b-octahydro-9-nitro-6-oxopyrido[2,1-a][2]benzazepine-4-carboxylic acid, diphenylmethyl ester (158 mg, 0.632 mmol) and proton sponge (138 mg, 0. 648 mmol) in methylene chloride (5 mL). Add a solution of (R)-2-trifluoromethanesulfonyl-4-phenylbutyric acid , diphenylmethyl ester (309 mg, 0.648 mmol) in methylene chloride (2 ml ). Stir at room temperature under an argon atmosphere for 26 hours. Purify by flash silica gel chromatography (30% ethyl acetate/hexane→50% ethyl acetate/hexane) to give the title compound as a yellow foam (178 mg, 67.2%).

Anal. Calcd for $C_{51}H_{47}N_3O_7$: C, 75.25; H, 5,82; N, 5.16; Found: C, 74.10; H, 5,82; N, 4.87.

Scheme A, Step e$_1$: [4S-[4α,7α(R*),12bβ]]-7-[(S-1-Carboxy-3-phenylpropyl)amino]-1,2,3,4,6,7,8,12b-octahydro-9-nitro-6-oxopyrido[2]benzazepine-4-carboxylic acid Dissolve [4S-[4α,7α(R*),12bβ]]-7-[[S-1-[carbodiphenylmethoxy]-3-phenylpropyl]amino]-1,2,3,4,6,7,8,12b-octahydro-9-nitro-6-oxopyrido[2,1-a][2]benzazepine-4-carboxylic acid, diphenylmethyl ester (39 mg, 0.045 mmol) in methylene chloride (1 mL). Add trifluoroacetic acid (1 mL) and anisole (0.2 mL). Allow to stand for 3 hours under an argon atmosphere. Partition between methylene chloride and 1N hydrochloric acid. Separate the aqueous phase and freeze dry. Purify by High Pressure Liquid Chromatography (elute with 25% methanol with 0.1% trifluoroacetic acid at 15 mL/min on a 22.5 cm×250 cm Vydac C-18 column) to give the title compound (18 mg, 72%).

EXAMPLE 2

[4S-[4α,7α(R*),12bβ]]-9-Amino-7-[(S-1-carboxy-3-phenylpropyl)amino]-1,2,3,4,6,7,8,12b-octahydro-6-oxopyrido[2,1-a][2]benzazepine-4-carboxylic acid, dihydrochloride Dissolve [4S-[4α7α(R*),12bβ]]-7-[[S-1-[carbodiphenylmethoxy]-3-phenylpropyl]amino]-1,2,3,4,6,7,8,12b-octahydro-9-nitro-6-oxopyrido[2,1-a][2]benzazepine-4-carboxylic acid, diphenylmethyl ester (52 mg, 0.064 mmol) in tetrahydrofuran (3 mL). Add 10% palladium/carbon (18 mg) and water (3 mL). Shake under 44 psi of hydrogen at room temperature for 20 hours. Filter and evaporate the solvent in vacuo. Take the residue up in 1N hydrochloric acid, filter then freeze dry to give the title compound (25 mg, 74%).

EXAMPLE 3

[4S-[4α,7α(R*),12bβ]]-7-[(S-1-Carboxy-3-phenylpropyl)amino]-1,2,3,4,6,7,8,12b-octahydro-11-nitro-6-oxopyrido[2,1-a][2]benzazepine-4-carboxylic acid Scheme A, Step b: [4S-[4α,7α(R*),12bβ]]-7-[1,3-Dihydro-1,3-dioxo-2H-isoindol-2-yl]-1,2,3,4,6,7,8,12b-octahydro-11-nitro-6-oxopyrido[2,1-a][2]benzazepine-4-carboxylic acid, diphenylmethyl ester dissolve [4S-[4α,7α(R*),12bβ]]-7-[1,3-dihydro-1,3-dioxo-2H-isoindol-2-yl]-1,2,3,4,6,7,8,12,b-octahydro-11-nitro-6-oxopyrido[2,1-a]benzazepine-4-carboxylic acid (795 mg, 1.77 mmol) in methylene chloride (2 mL). Add diphenyldiazomethane (350 mg, 1.78 mmol) and methylene chloride (5 mL). Let stand for 8 hours. Purify the residue by silica gel chromatography (35% ethyl acetate/hexane→50% ethyl acetate/hexane) to give the title compound as a white foam (756 mg, 69.4%).

Scheme A, Step c: [4S-[4α,7α(R*),12bβ]]-7-Amino-1,2,3,4,5,6,7,8,12b-octahydro-11-nitro6-oxopyrido[2,1-a][2]benzazepine-4-carboxylic acid, diphenylmethyl ester Slurry [4S-[4α,7α(R*),12bβ]]-7-dihydro-1,3-dioxo-2H-isoindol-2-yl]-1,2,3,4,6,7,8,12b-octahydro-11-nitro-6-oxopyrido[2,1-a][2]benzazepine-4-carboxylic acid, diphenylmethyl ester (756 mg, 1.23 mmol) in methanol (5 mL) and add hydrazine hydrate (4.0 mL of a 1M solution in methanol, 4.0 mmol). Stir at room temperature under an argon atmosphere for 10 minutes then warm to reflux for 90 minutes. Evaporate the solvent in vacuo and stir the residue with methylene chloride for 20 minutes. Filter and wash the filtrate with water, dry (MgSO$_4$) and evaporate the solvent in vacuo to give the title compound as a yellow film (610 mg, 00%).

Scheme A, Step b: [4S-[4α,7α(R*),12bβ]]-7-[[S-1-[Carbodiphenylmethoxy]-3-phenylpropyl]amino]-1,2,3,4,6,6,8,,12b-octahydro-11-nitro-6-oxopyrido[2,1-a][2]benzazepine-4-carboxylic acid, diphenylmethyl ester Dissolve [4S-[4α,7α(R*),12bβ]]-7-amino-1,2,3,4,6,7,8,12b-octahydro-11-nitro-6-oxopyrido[2,1-a][2-benzazepine-4-carboxylic acid, diphenylmethyl ester (90 mg, 0.18 mmol) and proton sponge (250 mg, 1.12 mmol) in methylene chloride (5 mL). Add a solution of (R)-2-trifluoromethanesulfonyl-4-phenylbutyric acid, diphenylmethyl ester (520 mg, 1.17 mmol) in methylene chloride (6 ml). Stir at room temperature under an argon atmosphere for 22 hours. Dilute with cyclohexane (20 mL) and filter. Purify by silica gel chromatography (30% ethyl acetate/hexane) to give the title compound (105 mg, 72%).

Anal. Calcd for $C_{51}H_{47}N_3O_7$: C, 75.25; H, 5.82; N, 5.16; Found: C, 74.84; H, 5.84; N, 4.84.

Scheme A, Step e$_1$: [bS-[4α,7α(R*),12bβ]]-7-(S-1-Carboxy-3-phenylpropyl)amino]-1,2,3,4,6,7,8,12b-octahydro-11-nitro-6-oxopyrido[2,1-a][2]benzazepine-4-carboxylic acid, hydrochloride dissolve [4S-[4α,7α(R*),12bβ]]-7-[[S-1-[carbodiphenylmethoxy]-3-phenylpropyl]amino]-

1,2,3,4,6,7,812b-octahydro-11-nitro-6-oxopyrido[2,1-a][2]benzazepine-4-carboxylic acid, diphenylmethyl ester (52 mg, 0.063 mmol) in methylene chloride (2 mL). Add trifluoroacetic acid (1 mL) and anisole (0.2 mL). Allow to stand for 2 hours under an argon atmosphere. Partition between methylene chloride and 9:1 water/methanol. Separate the organic phase and extract with additional 9:1 water/methanol (10 mL). Combine the aqueous phases and wash with methylene chloride (3×10 mL). Separate the aqueous phase and freeze dry to give the title compound as a white powder (24.6 mg, 74.5%).

EXAMPLE 4

[4S-[4α,7α(R*),12bβ]]-11-Amino-7-[(S-1-carboxy-3-phenylpropyl)amino]-1,2,3,4,6,7,8,12b-octahydro-6-oxopyrido[2,1-][2]benzazepine-4-carboxylic acid, dihydrochloride Dissolve [4S-[4α,7α(R*),12bβ]]-7-[[S-1-[carbodiphenylmethoxy]-3-phenylpropyl]amino]-1,2,3,4,6,7,8,12b-octahydro-11-nitro-6-oxopyrido[2,1-a][2]benzazepine-4-carboxylic acid, diphenylmethyl ester (56 mg, 0.06 mmol) in tetrahydrofuran (6 mL). Add 10% palladium/carbon (20 mg) and water (3 mL). Shake under 45 psi of hydrogen at room temperature for 5 hours. Filter and partition the filtrate between in 1N hydrochloric acid and methylene chloride. Separate the aqueous phase and freeze dry to give the title compound (35.3 mg, 98%).

EXAMPLE 5

[4S-[4α,7α(R*),12bβ]]-7-[(S-1-Carbethoxy-3-phenylpropyl)amino]-1,2,3,4,6,7,8,12b-octahydro-9-nitro-6-oxopyrido[2,1-a][2]benzazepine-4-carboxylic acid Scheme B, Step a: [4S-[4α,7α(R*),12bβ]]-7-[(S-1-Carbethoxy-3-phenylpropyl)amino]-1,2,3,4,6,7,8,12b-octahydro-9-nitro-6-oxopyrido[2,1-][2]benzazepine-4-carboxylic acid, diphenylmethyl ester Dissolve [4S-[4α,7α(R*),12bβ]]-7-amino-1,2,3,4,6,7,8,12b-octahydro-9-nitro-6-oxopyrido[2,1-][2]benzazepine-4-carboxylic acid, diphenylmethyl ester (596 mg, 1.23 mmol) and proton sponge (296 mg, 1.25 mmol) in methylene chloride (10 mL). Add a solution of (R)-2-trifluoromethanesulfonyl-4-phenylbutyric acid, ethyl ester (428 mg, 1.25 mmol) in methylene chloride (6 ml). Stir at room temperature under an argon atmosphere overnight. Purify by silica gel chromatography to give the title compound.

Scheme B, Step b₁: [4S-[4α,7α(R*),12bβ]]-7-[(S-1-Carbethoxy-3-phenylpropyl)amino]-1,2,3,4,6,7,8,12b-octahydro-9-nitro-6-oxopyrido[2,1-a][2]benzazepine-4-carboxylic acid Dissolve [4S-[4α,7α(R*),12bβ]]-7-[(S-1-carbethoxy-3-phenylpropyl)amino]-1,2,3,4,6,7,8,12b-octahydro-9-nitro-6-oxopyrido[2,1-a][2]benzazepine-4-carboxylic acid, diphenylmethyl ester (42.5 mg, 0.063 mmol) in methylene chloride (2 mL). Add trifluoroacetic acid (1 mL) and anisole (0.2 mL). Allow to stand for 2 hours under an argon atmosphere. Partition between methylene chloride and 9:1 water/methanol. Separate the organic phase and extract with additional 9:1 water/methanol (10 mL). Combine the aqueous phases and wash with methylene chloride (3×10 mL ). Separate the aqueous phase and freeze dry to give the title compound.

EXAMPLE 6

4s-[4α,7α(R*)12bβ]]-9-Amino-7-[(1-carbethoxy-3-phenylpropyl)amino]-1,2,3,4,6,7,8,12b-octahydro-6-oxopyrido[2,1-[[2]benzazepine-4-carboxylic acid dihydrochloride Dissolve [4S-[4α,7α(R*),12bβ]]-7-[(S-1-carbethoxy-3-phenylpropyl)amino]-1,2,3,4,6,7,87,12b-octahydro-9-nitro-6-oxopyrido[2,1-a][2]benzazepine-4-carboxylic acid, diphenylmethyl ester (260 mg, 385 mmol) in ethanol (7 mL). Add 10% palladium/carbon under an atmosphere of carbon dioxide. Shake under 42 psi of hydrogen at room temperature for 5.5 hours. Filter and evaporate the solvent in vacuo. Take up the residue in 1N hydrochloric acid (2 mL) and dilute with water (10 mL). Wash with methylene chloride (3×5 mL) and freeze dry the aqueous phase to give the title compound.

EXAMPLE 7

[4S-[4α,7α(R*),12bβ]]-7-[(S-1-Carbethoxy-3-phenylpropyl)amino[-1,2,3,4,6,7,8,12b-octahydro-1-nitro-6-oxopyrido[2,1-a][2]benzazepine-4-carboxylic acid Scheme B, Step a: [4S-[4α,7α(R*),12bβ]]-7-[(S-1-Carbethoxy-3-phenylpropyl)amino]-1,2,3,4,6,7,8,12b-octahydro-11-nitro-6-oxopyrido[2,1-a][2]benzazepine-4-carboxylic acid, diphenylmethyl ester Dissolve [4S-[4α,7α(R*),12bβ]]-7-amino-1,2,3,4,6,7,8,12b-octahydro-11-nitro-6-oxopyrido[2,1-a][2]benzazepine-4-carboxylic acid, diphenylmethyl ester (596 mg, 1.23 mmol) and proton sponge (296 mg, 1.25 mmol) in methylene chloride (10 mL). Add a solution of (R)-2-trifluoromethanesulfonyl-4-phenylbutyric acid, ethyl ester (428 mg, 1.25 mmol) in methylene chloride (6 ml). Stir at room temperature under an argon atmosphere overnight. Purify by silica gel chromatography (35% ethyl acetate/hexane) to give the title compound as a light yellow foam (591 mg, 71.1%); mp 75°–80° C.

Anal. Calcd for $C_{40}H_{41}N_3O_7$: C, 71.09; H, 6.12; N, 6.22; Found: C, 70.81; H, 5.98; N, 6.13.

Scheme B, Step b₁: [4S-[4α,7α(R*),12bβ]]-7,[(S-1-Carbethoxy-3-phenylpropyl)amino]-1,2,3,4,6,7,8,12b-octahydro-11-nitro-6-oxopyrido]2,1-a]][2]benzazepine-4-carboxylic acid Dissolve [4S-[4α,7α(R*),12bβ]]-7-[(S-1-carbethoxy-3-phenylpropyl)amino]-1,2,3,4,6,7,8,12b-octahydro-11-nitro-6oxopyrido[2,1-a][2]benzazepine-4-carboxylic acid, diphenylmethyl ester (42.5 mg, 0.063 mmol) in methylene chloride (2 mL). Add trifluoroacetic acid (1 mL) and anisole (0.2 mL). Allow to stand for 2 hours under an argon atmosphere. Partition between methylene chloride and 9:1 water/methanol. Separate the organic phase and extract with additional 9:1 water/methanol (10 mL). Combine the aqueous phases and wash with methylene chloride (3×10 mL). Separate the aqueous phase and freeze dry to give the title compound.

EXAMPLE 8

[4S-[4α,7α(R*),12bβ]]11-Amino-7-[(S-1-carbethoxy-3-phenylpropyl)amino]-1,2,3,4,6,7,8,12b-octahydro-6-oxopyrido[2,1-a][2]benzazepine-4-carboxylic acid, dihydrochloride Dissolve [4S-[4α,7α(R*),12bβ]]-7-[(S-1-carbethoxy-3-phenylpropyl)amino]-1,2,3,4,6,7 ,8,12b-octahydro-11- nitro-6oxopyrido[2,1-a][2]benzazepine-4-carboxylic acid diphenylmethyl ester (260 mg, 38 5 mmol) in ethanol (7 mL). Add 10% palladium/carbon under an atmosphere of carbon dioxide. Shake under 42 psi of hydrogen at room temperature for 5.5 hours. Filter and evaporate the solvent in vacuo. Take up the residue in 1N hydrochloric acid (2 mL) and dilute with water (10 mL). Wash with methylene chloride (3×5 mL) and freeze dry the aqueous phase to give the title compound as yellow crystals (178 mg, 83.6%); mp 175°–95° C.

EXAMPLE 9

[4S-[4α,7α(R*),12bβ]]-7-[(S-1-Carboxy-3-phenylpropyl)amino]-1,2,3,4,6,7,8,12b-hexahydro-9-nitro-6-oxo-1H-[1,4]-oxazino[3,4a][2]benzazepine-4-carboxylic acid Scheme C, step a: N-[2-(1,3-Dihydro-1,3-dioxo-2H-isoindol-2-yl)-1-oxo-3-phenylpropyl]-L-serine, methyl ester Slurry N-phthaloyl-(S)-phenylalanine (90 g, 0.3 mol) in methylene chloride (450 mL) and add, by dropwise addition, oxalyl chloride (54 mL, 0.62 mol). Place under a dry atmosphere (CaSO₄ tube) and treat with dimethylformamide (10 μL). Stir for 5 hours, filter and concentrate in vacuo to give N-phthaloyl-(S)-phenylalanine, acid chloride as an off white amorphous solid.

Dissolve serine methyl ester hydrochloride (56 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO₄). Evaporate the solvent in vacuo to give an oil. Purify by silica gel chromatography (gradient 50% ethyl acetate/hexane to ethyl acetate) to give the title compound (80.8 g, 67%) mp 129°–132° C.

Scheme C, step b: N-[2-(1,3-Dihydro-1,3-dioxo-2H-isoindol-2-yl)-1-oxo-3-phenylpropyl]-O-2-propenyl-L-serine, methyl ester Dissolve N-[2-(1,3-dihydro-1,3-dioxo-2H-isoindol-2-yl)-1-oxo-3-phenylpropyl]-L-serine, methyl ester (25 g, 63 mmol) in methylene chloride/cyclohexane (1:1, 600 mL). Add allyl trichloroacetimidate (26 g, 128 mmol) and trifluoromethanesulfonic acid (5 mL), 56.6 mmol). Stir at room temperature under a nitrogen atmosphere for 5 hours and dilute with methylene chloride. Wash with saturated aqueous sodium hydrogen carbonate, water, dry (MgSO₄) and evaporate the solvent in vacuo. Purify by silica gel chromatography (gradient 2 0% ethyl acetate/hexane to 35% ethyl acetate/hexane) to give the title compound; mp 95°–97° C.

Scheme C, step C: [S-(R*, R*)]-N-[2-(1,3-Dihydro-1,3-dioxo2H-isoindol-2-yl)-1-oxo-3-phenylpropyl]-3,4-dihydro-2H-1,4-oxazine-3-carboxylic acid, methyl ester Dissolve N-[2-(1,3-dihydro-1,3-dioxo-2H-isoindol-2-yl)-1-oxo-3-phenylpropyl]-O-2-propenyl-L-serine, methyl ester (13 g, 29.8 mmol) in methylene chloride /methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methyl sulfide (60 mL, 0.82 mol) and allow to warm to room temperature. Stir at room temperature for 2.5 hours, evaporate the solvent in vacuo and dissolve the residue in ethyl acetate (200 mL). Wash with water, saturated sodium chloride, dry (MgSO₄) and evaporate the solvent in vacuo to give the intermediate N-[2-(1,3-dihydro-1,3-dioxo-2H-isoindol-2-yl)-1-oxo-3-phenylpropyl]-O-2-oxoethyl-L-serine, methyl ester as a foam (13.6 g).

Dissolve N-[2-(1,3-dihydro-1,3-dioxo-2H-isoindol-2-yl)-1-oxo-3-phenylpropyl]-O-2-oxoethyl-L-serine, methyl ester (13.6 g) in methylene chloride/trifluoroacetic acid (10:1/330 mL). Stir at room temperature for 2.5 hours and evaporate the solvent in vacuo. Purify by silica gel chromatography (35% ethyl acetate/hexane) and recrystallize (ethyl acetate/hexane) to give the title compound (8.52 g, 68%); mp 70°–72° C.

Scheme C, step d: [4S-[4α, 7α(R*),12bβ]]-7-[(1,3-Dihydro-1,3-dioxo-2H-isoindol-2-yl)]-3,4,6,7,8,12b, hexahydro-6-oxo-1H-[1,4]-oxazino[3,4-a][2]benzazepine-4-carboxylic acid Dissolve [S-(R*, R*)]-N-[2-(1,3-dihydro-1,3-dioxo-2H-isoindol-2-yl)-1-oxo-3-phenylpropyl]-3,4-dihydro-2H-1,4-oxazine-3-carboxylic acid, methyl ester (2.5 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride and dry (MgSO₄). Evaporate the solvent in vacuo and dry the residue under high vacuum at 56° C. for 24 hours to give the title compound (1.75 g, 73%).

Scheme A, Step a: [4S-[4α,7α(R*),12bβ]]-7-[1,3-Dihydro-1,3-dioxo-2H-isoindol-2-yl]-3,4,6,7,8,12b-hexahydro-9-nitro-6-oxo-1H-[1,4]-oxazino[3,4-a][2]benzazepine-4-carboxylic acid and [4S-[4α,7α(R*),12bβ]]-7-[-1,3-dihydro-1,3-dioxo-2H-isoindol-2-yl]-3,4,6,7,8,12b-hexaahydro-11-nitro-6-oxo-1H-[1,4]-oxazino[3,4-a][2]benzazepine-4-carboxylic acid Mix trifluromethanesulfonic acid (4 ml, 45 mmol) and nitric acid (1 ml, 22 mmol) and anhydrous methylene chloride (100 mL). Cool to −78° C. and add, by dropwise addition, a solution of [4S-[4α,7α(R*),12bβ]]-7-[1,3-dihydro-1,3-dioxo-2H-isoindol-2-yl]-3,4,6,7,8,12b-hexahydro-6-oxo-1H-[1,4]-oxazino[3,4-a][2]benzazepine-4-carboxylic acid (1.94 g, 4.78 mmol) in methylene chloride (60 mL). Stir at −78° C. for 20 minutes, allow to warm to room temperature and stir under a nitrogen atmosphere for 3.5 hours. Wash with water, dry (MgSO₄) and evaporate the solvent in vacuo to give yellow foam (2.3 g). Take up in ethyl acetate, wash with brine (3×), dry (MgSO₄) and evaporate the solvent in vacuo to give a yellow foam. Pufiy and separate by flash silica gel chromatography 1:1:0.04 ethyl acetate/-hexane/acetic acid) to give a small amount of the 9-nitro title compound and 1.02 g of the 11-nitro title compound (47%).

Scheme A, Step b: [4S-[4α,7α(R*),12bβ]]-7-[1,3-Dihydro-1,3-dioxo-2H-isoindol-2-yl]-3,4,6,7,8,12b-hexahydro-9-nitro-6-oxo-1H-[1,4]-oxazino[3,4-a ][2]benzazepine-4-carboxylic acid, diphenylmethyl ester Dissolve [4S-[4α,7α(R*),12bβ]]-7-[1,3-dihydro-1,3-dioxo-2H-isoindol-2-yl]-3,4,6,7,8,12b-hexahydro-9-nitro-6-oxo-1H-[1,4]-oxazino[3,4-a][2]benzazepine-4-carboxylic acid (1.50 mmol) in methylene chloride (1 mL). Add diphenyldiazomethane (291 mg, 1.50 mmol) and let stand for several days in which time the methylene chloride evaporates. Purify the residue by silica gel chromatography to give the title compound.

Scheme A, Step c: [4S-[4α,7α(R*),12bβ]]-7-Amino-3,4,6,7,8,12b-hexahydro-9-nitro-6-oxo-1H-[1,4]-oxazino-[3,4-a][2]benzazepine-4-carboxylic acid, diphenylmethyl ester Slurry [4S-[4α,7α(R*),12bβ]]-7-[1,3-dihydro-1,3-dioxo-2H-isoindol-2-yl]-3, 4,6,7,8,12b-hexahydro-9-nitro-6-oxo-1H-[1,4]-oxazino[3,4-a][2]benzazepine-4-carboxylic acid, diphenylmethyl ester (600 mg, 0.97 mmol) in methanol (5 mL) and add hydrazine hydrate (2.0 mL of a 1M solution in methanol, 2.0 mmol). Stir at room temperature under an argon atmosphere for 4 hours. Add methanol (20 mL) and reflux for 1 hour, then stir at room temperature overnight. Evaporate the solvent in vacuo, take up the residue in ethyl acetate and filter. Wash with filtrate with water (3×) and brine. Dry (MgSO4) and evaporate the solvent in vacuo to give the title compound (473 mg, 99.5%).

Scheme A, Step d: [4S-[4α,7α(R*),12bβ]]-7-[[S-1-[Carbodiphenylmethoxy]-3-phenylpropyl]amino]-3,4,6,7,8,12b-hexahydro-9-nitro-6-oxo-1H-[4]-oxazino[3,4-a][2]benzazepine-4-carboxylic acid, diphenylmethyl ester Dissolve [4S-[4α,7α(R*),12bβ]]-7-amino-3,4,6,7,8,12b-hexahydro-9-nitro-6-oxo-1H-[1,4]-oxazino[3,4-a][2]benzazepine-4-carboxylic acid, diphenylmethyl ester (0. 632 mmol ) and proton sponge (138 mg, 0.648 mmol) in methylene chloride (5 mL). Add a solution of (R)-2-trifluoromethanesulfonyl-4-phenylbutyric acid, diphenylmethyl ester (309 mg, 0.648 mmol) in methylene chloride (2 ml). Stir at room temperature under an argon atmosphere for 26 hours. Purify by flash silica gel chromatography to give the title compound.

Scheme A, Step e1: [4S-[4α,7α(R*),12bβ]]-7-[(S-1-Carboxy-3-phenylpropyl)amino]-3,4,6,7,8,12b-hexahydro-9-nitro-6-oxo-1H-[1,4]-oxazino[3,4-a][2]benzazepine-4-carboxylic acid Dissolve [4S-[4α,7α(R*),12bβ]]-7-[[S-1-[(diphenylmethoxy)carbonyl]-3-phenylpropyl]amino]-3,4,6,7,8,12b-hexahydro-9-nitro-6-oxo-1H-[1,4]-oxazino[3,4-a][2]benzazepine-4-carboxylic acid, diphenylmethyl ester (0.045 mmol) in methylene chloride (1 mL). Add trifluoroacetic acid (1 mL) and anisole (0.2 mL). Allow to stand for 3 hours under an argon atmosphere. Partition between methylene chloride and 1N hydrochloric acid. Separate the aqueous phase and freeze dry. Purify by High Pressure Liquid Chromatography to give the title compound.

EXAMPLE 10

[4S-[4α,7α(R*),12bβ]]-7-[(S-1-Carboxy-3-phenylpropyl)amino ]-3,4,6,7,8,12b-hexahydro-9-nitro-6-oxo-1H-[1,4]-thiazino[3,4-a][2]benzazepine-4-carboxylic acid Scheme A, Step a: [4S-[4α,7α(R*),12bβ]]-7-[1,3-Dihydro-1,3-dioxo-2H-isoindol-2-yl]-3,4,6,7,8,12b-hexahydro-9-nitro-6-oxo-1H-[1,4]-thiazino[3,4,-a][2]benzazepine-4-carboxylic acid and [4S-[4α,7α(R*),12bβ]]-7-[1,3-dihydro-1,3-dioxo-2H-isoindol-2-yl]-3,4,6,7,8,12b-hexaahydro-11-nitro-6-oxo-1H-[1,4]-thiazino[3,4-a][2]benzazepine-4-carboxylic acid Dissolve [4S-[4α,7α(R*),12bβ]]-7-[1,3-dihydro-1,3-dioxo-2H-isoindol-2-yl]-3,4,6,7,8,12b -hexahydro-6-oxo-1H-[1,4]-thiazino[3,4-a][2]benzazepine-4-carboxylic acid, methyl ester (0.233 mmol) in ethanol (4 mL) and treat with trifluoromethanesulfonic acid (0.5 mL). Stir under nitrogen atmosphere until hydrolysis is complete, pour into water, extract the aqueous phases with ethyl acetate (2×) and wash the combined organic phases with water, then with saturated sodium chloride. Dry (MgSO4), evaporate the solvent in vacuo and purify by silica gel chromatography to give [4S-[4α,7α(R*), 12bβ]]-7-[1,3-dihydro-1,3-dioxo-2H-isoindol-2-yl]-3,4,6,7,8,12b-hexahydro-6-oxo-1H-[1,4]-thiazino[3,4-a][2]benzazepine-4-carboxylic acid.

Mix trifluromethanesulfonic acid (4 ml, 45 mmol) and nitric acid (1 ml, 22 mmol ) and anhydrous methylene chloride (100 mL). Cool to −78° C. and add, by dropwise addition, a solution of [4S-[4α,7α(R*),12bβ]]-7-[1,3-dihydro-1,3-dioxo-2H-isoindol-2-yl]-3,4,6,7,8,12b-hexahydro-6-oxo-1H-[1,4]-thiazino[3,4-a][2]benzazepine-4-carboxylic acid (4.78 mmol) in methylene chloride (60 mL). Stir at −78° C. for 20 minutes, allow to warm to room temperature and stir under a nitrogen atmosphere for 3.5 hours. Wash with water, dry (MgSO4) and evaporate the solvent in vacuo. Purify and separate by flash silica gel chromatography to give the 11-nitro title compound and the 9-nitro title compound.

Scheme A, Step b: [4S-[4α,7α(R*),12bβ]]-7-[1,3-Dihydro-1,3-dioxo-2H-isoindol-2-yl]-3,4,6,7,8,12b-hexahydro-9-nitro-6-oxo-1H-[1,4]-thiazino[3,4-a][2]benzazepine-4-carboxylic acid, diphenylmethyl ester Dissolve [4S-[4α,7α(R*),12bβ]]-7-[1,3-dihydro-1,3-dioxo-2H-isoindol-2-yl]-3,4,6,7,8,12b-hexahydro-9-nitro-6-oxo-1H-[1,4]-thiazino[3,4-a][2]benzazepine-4-carboxylic acid (1.50 mmol) in methylene chloride (1 mL). Add diphenyldiazomethane (291 mg, 1.50 mmol) and let stand for several days in which time the methylene chloride evaporates. Purify the residue by silica gel chromatography to give the title compound.

Scheme A, Step C: [4S-[4α,7α(R*),12bβ]]-7-Amino-3,4,6,7,8,12b-hexahydro-9-nitro-6-oxo-1H-[1,4]-thiazino[3,4-a][2]benzazepine-4-carboxylic acid, diphenylmethyl ester Slurry [4S-[4α,7α(R*),12bβ]]-7-[1,3-dihydro-1,3-dioxo-2H-isoindol-2-yl]-3,4,6,7,8,12b-hexahydro-9-nitro-6-oxo-1H-[1,4]-thiazino[3,4-a ][2]benzazepine-4-carboxylic acid, diphenylmethyl ester (0.324 mmol) in methanol (6 mL) and add hydrazine hydrate (1.0 mL of a 1M solution in methanol, 1.0 mmol). Stir at room temperature under an argon atmosphere for 20 hours. Dilute with methylene chloride (30 mL) and stir for 2 hours. Filter and concentrate in vacuo. Take up the residue in methylene chloride and filter again. Wash the filtrate with water, dry (MgSO4) and evaporate the solvent in vacuo to give the title compound.

Scheme A, Step d: [4S-[4α,7α(R*),12bβ]]-7-[[S-1-[Carbodiphenylmethoxy]-3-phenylpropyl]amino]-3,4,6,7,8,12b-hexahydro-9-nitro-6-oxo-1H-[1,4]-thiazino[3,4-a][2]benzazepine-4-carboxylic acid, diphenyl methyl ester Dissolve [4S-[4α,7α(R*),12bβ]]-7-amino-3,4,6,7,8,12b-hexahydro-9-nitro-6-oxo-1H-[1,4]-thiazino[3,4-a][2]benzazepine-4-carboxylic acid, diphenylmethyl ester (0.632 mmol) and proton sponge (138 mg, 0.648 mmol) in methylene chloride (5 mL). Add a solution of (R)-2-trifluoromethanesulfonyl-4-phenylbutyric acid, diphenylmethyl ester (309 mg, 0.648 mmol) in methylene chloride (2 ml). Stir at room temperature under an argon atmosphere for 26 hours. Purify by flash silica gel chromatography to give the title compound.

Scheme A, Step e₁: 4S-[4α,7α(R*),12bβ]]-7-[(S-1-Carboxy-3-phenylpropyl)amino]-3,4,6,7,8,12b-hexahydro-9-nitro-6-oxo-1H-[1,4]-thiazino[3,4-a][2]benzazepine-4-carboxylic acid Dissolve [4S-[4α,7α(R*),12bβ]]-7-[[S-1-[carbodiphenylmethoxy]-3-phenylpropyl]amino]-3,4,6,7,8,12b-hexahydro-9-nitro-6-oxo-1H-[1,4]-thiazino[3,4-a][2]benzazepine-4-carboxylic acid, diphenylmethyl ester (0.045 mmol) in methylene chloride (1 mL). Add trifluoroacetic acid (1 mL) and anisole (0.2 mL). Allow to stand for 3 hours under an argon atmosphere. Partition between methylene chloride and 1N hydrochloric acid. Separate the aqueous phase and freeze dry. Purify by High Pressure Liquid Chromatography to give the title compound.

EXAMPLE 11

[4S-[4α,7α(R*),12bβ]],7-[(S-1-Carboxy-3-phenylpropyl)amino]-3,4,6,7,8,12b-hexahydro-9-nitro-6-oxo-1H-[1,4]-N⁴-trifluoroacetyl-azazino[3,4-][2]benzazepine-4-carboxylic acid Scheme D, step a: N-[2-(1,3-Dihydro-1,3-dioxo-2H-isoindol-2,yl)-1-oxo-3-phenylpropyl]-(S)-3-[(trifluoroacetyl-2-propenyl)amino]-2-amino-propionic acid, methyl ester Dissolve Nᵅ-(carbobenzyloxy)-β-(amino)-L-alanine, methyl ester (2.27 mmol) in anhydrous tetrahydrofuran (15 mL). Treat with pyridine (183 μL, 2.27 mmol) followed by trifluoroacetic anhydride (321 μL, 2.27 mmol) and stir at ambient temperature for 1 hours. Add additional pyridine (180 μL) and trifluoroacetic anhydride (320 μL). Allow to stand overnight, partition between ethyl ether and water. Separate the organic phase, dry (MgSO₄) and evaporate the solvent in vacuo to give Nᵅ-(carbobenzyloxy)-β-(trifluoroacetyl)-L-alanine, methyl ester.

Suspend sodium hydride (4.8 g, 0.2 mol) in anhydrous dimethylformamide (100 mL), cool to 0° C. and place under a nitrogen atmosphere. Add, by dropwise addition, a solution of Nᵅ-(carbobenzyloxy)-β-(trifluoroacetyl)-L-alanine, methyl ester (0.2 mol) in dimethylformamide. Stir until evolution of hydrogen ceases. Add, by dropwise addition, a solution of allyl bromide (0.2 mol) in dimethylformamide (100 mL). Stir overnight at room temperature then carefully quench with saturated ammonium chloride. Extract into ethyl acetate, dry (MgSO₄) and evaporate the solvent in vacuo. Purify by silica gel chromatography to give Nᵅ-(carbobenzyloxy)-β-(trifluoroacetyl-allylamino)-L-alanine, methyl ester.

Place boron tribromide (215 mg, 0.86 mmol) in a flask and cool to 0° C. Cautiously add trifluoroacetic acid (5 mL) with stirring. Evaporate the solvent to give boron tris(trifluoroacetate).

Dissolve boron tris(trifluoroacetate) (0.3 g, 0.86 mmol) in trifluoroacetic acid (10 mL) and add Nᵅ-(carbobenzyloxy)-β-(trifluoroacetyl-allylamino)-L-alanine, methyl ester (105 mg, 0.27 mmol). Stir under an argon atmosphere for 1 hour then evaporate the solvent in vacuo at room temperature. Add methanol and evaporate repeatedly. Purify by silica gel chromatography to give β-(trifluoroacetyl-allylamino)-L-alanine, methyl ester, hydrochloride.

Dissolve β-(trifluoroacetyl-allylamino)-L-alanine, methyl ester, hydrochloride (104.8 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride (108.7 g, 0.36 mol) in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO₄). Evaporate the solvent in vacuo to give an oil. Purify by silica gel chromatography to give the title compound.

Scheme D, step b: [S-(R*, R*)]-N-[2-(1.3-Dihydro-1,3-dioxo-2H-isoindol-2-yl)-1-oxo-3-phenylpropyl]-3,4-dihydro-2H-4-trifluoroacetyl-1,4-azazine-3-carboxylic acid, methyl ester Dissolve N-[2-(1,3-dihydro-1,3-dioxo-2H-isoindol-2-yl)-1-oxo-3-phenyl propyl]-(S)-3-[(trifluoroacetyl-2propenyl)amino]-2-amino-propionic acid, methyl ester (15.8 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methyl sulfide (60 mL, 0.82 mol) and allow to warm to room temperature. Stir at room temperature for 2.5 hours, evaporate the solvent in vacuo and dissolve the residue in ethyl acetate (200 mL). Wash with water, saturated sodium chloride, dry (MgSO₄) and evaporate the solvent in vacuo to give the intermediate N-[2-(1,3-dihydro-1,3-dioxo-2H-isoindol-2-yl)-1-oxo-3-phenylpropyl-]-(S)-3[(trifluoroacetyl-2-oxoethyl-)amino]-2-amino-propionic acid, methyl ester.

Dissolve N-[2-(1,3-dihydro-1,3-dioxo-2H-isoindol-2-yl)-1-oxo-3-phenylpropyl]-(S)-3-[(trifluoroacetyl-2-oxoethyl)amino-propionic acid, methyl ester (15.9 g, 29.8 mmol) in methylene chloride/trifluoroacetic acid (10:1/330 mL). Stir at room temperature for 2.5 hours and evaporate the solvent in vacuo. Purify by silica gel chromatography to give the title compound.

Scheme D, step c: [4S-[4α, 7α(R*),12bβ]]-7-[(1,3-Dihydro-1,3-dioxo-2H-isoindol-2-yl)]-3,4,6,7,8,12b-hexahydro-6-oxo-1H-[1,4]-N⁴-trifluoroacetyl-azazino[3,4-a][2]benzazepine-4-carboxylic acid Dissolve [S-(R*, R*)]-N-[2-(1,3-dihydro-1,3-dioxo-2H-isoindol-2-yl)-1-oxo-3-phenylpropyl]-3,4-dihydro-2H-4-trifluoroacetyl-1,4-azazine-3-carboxylic acid, methyl ester (3.04 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride arid dry (MgSO$_4$). Evaporate the solvent in vacuo and dry the residue under high vacuum at 56° C. for 24 hours to give the title compound.

Scheme A, step a: [4S-[4α,7α(R*),12bβ]]-7-[1,3-dihydro-1,3-dioxo-2H-isoindol-2-yl ]-3,4,6,7,8,12b-hexahydro-9-nitro-6-oxo-1H-[1,4]-N$^4$-trifluoroacetyl-azazino[3,4-a][2]benzazepine-4-carboxylic acid and [4S-[4α,7α(R*),12bβ]]-7-[1,3-dihydro-1,3-dioxo-2H-isoindol-2-yl]-3,4,6,7,8,12b-hexahydro-11-nitro-6-oxo-1H-[1,4]-N$^4$-trifluoroacetyl-azazino[3,4-a][2]benzazepine-4-carboxylic acid Dissolve [4S-[4α,7α(R*),12bβ]]-7-[1,3-dihydro-1,3-dioxo-2H-isoindol-2-yl]-3,4,6,7,8,12b-hexahydro-6-oxo-1H-[1,4]-N$^4$-trifluoroacetyl-azazino[3,4-a][2]benzazepine-4-carboxylic acid (3.5 mmol) in methylene chloride (10 mL) and cool to −60° C. Add, by dropwise addition, a solution of nitronium tetrafluoroborate (25 mL of a 0.5M solution in sulfolane, 12.5 mmol) in methylene chloride (15 mL). Warm slowly to 10° C. over 34 hours. Partition between methylene chloride (75 mL) and water (75 mL). Separate the aqueous phase and extract with methylene chloride (50 mL). Combine the organic phases, dry (MgSO$_4$) and evaporate the solvent in vacuo. Purify and separate by flash silica gel chromatography to give the 11-nitro title compound and the 9-nitro title compound.

Scheme A, Step b: [4S-[4α,7α(R*),12bβ]]-7-[1,3-Dihydro-1,3-dioxo-2H-isoindol-2-yl]-3,4,6,7,8,12b-hexahydro-9-nitro-6-oxo-1H-[1,4]-N$^4$-trifluoroacetyl-azazino[3,4-a][2]benzazepine-4-carboxylic acid, diphenylmethyl ester Dissolve [4S-[4α,7α(R*),12bβ]]-7-[1,3-dihydro-1,3-dioxo-2H-isoindol-2-yl]-3,4,6,7,8,12b-hexahydro-9-nitro-6-oxo-1H-[1,4]-N$^4$-trifluoroacetyl-azazino[3,4-a][2]benzazepine-4-carboxylic acid (1.50 mmol) in methylene chloride (1 mL). Add diphenyldiazomethane (291 mg, 1.50 mmol) and let stand for several days in which time the methylene chloride evaporates. Purify the residue by silica gel chromatography to give the title compound.

Scheme A, Step c: [4S-[4α,7α(R*),12bβ]]-7-Amino-3,4,6,7,8,12b-hexahydro-9-nitro-6-oxo-1H-[1,4]-N$^4$-trifluoroacetyl-azazino[3,4-a][2]benzazepine-4-carboxylic acids. diphenylmethyl ester Slurry [4S-[4α,7α(R*),12bβ]]-7-[1,3-dihydro-1,3-dioxo-2H-isoindol-2-yl]-3,4,6,7,8,12b-hexahydro-9-nitro-6-oxo-1H-[1,4]-N$^4$-trifluoroacetyl-azazino[3,4-a][2]benzazepine-4-carboxylic acid, diphenylmethyl ester (0.324 mmol) in methanol (6 mL) and add hydrazine hydrate (1.0 mL of a 1M solution in methanol, 1.0 mmol). Stir at room temperature under an argon atmosphere for 20 hours. Dilute with methylene chloride (30 mL) and stir for 2 hours. Filter and concentrate in vacuo. Take up the residue in methylene chloride and filter again. Wash the filtrate with water, dry (MgSO$_4$) and evaporate the solvent in vacuo to give the title compound.

Scheme A, Step d: [4S-[4α,7α(R*),12bβ]]-7-[[S-1[Carbodiphenylmethoxy]-3-phenylpropyl-]amino]-3,4,6,7,8,12b-hexahydro-9-nitro-6-oxo-1H-[1,4]-N$^4$-trifluoroacetyl-azazino[3,4-a][2]benzazepine-4-carboxylic acid, diphenylmethyl ester Dissolve [4S-[4α,7α(R*),12bβ]]-7-amino-3,4,6,7,8,12b-hexahydro-9-nitro-6-oxo-1H-[1,4]-N$^4$-trifluoroacetyl-azazino[3,4-a][2]benzazepine-4-carboxylic acid, diphenylmethyl ester (0.632 mmol) and proton sponge (138 mg, 0.648 mmol) in methylene chloride (5 mL). Add a solution of (R)-2-trifluoromethanesulfonyl-4-phenylbutyric acid, diphenylmethyl ester (309 mg, 0.648 mmol) in methylene chloride (2 ml). Stir at room temperature under an argon atmosphere for 26 hours. Purify by flash silica gel chromatography to give the title compound.

Scheme A, Step e$_1$: [4S-[4α,7α(R*),12bβ]]-7-[(S-1-Carboxy-3-phenylpropyl)amino]-3,4,6,7,8,12b-hexahydro-9-nitro-6-oxo-1H-[1,4]-N$^4$-trifluoroacetyl-azazino[3,4-a][2]benzazepine-4-carboxylic acid Dissolve [4S-[4α,7α(R*),12bβ]]07-[[S-1-[carbodiphenylmethoxy]-3-phenylpropyl]amino]-3,4,6,7,8,12b-hexahydro-9-nitro-6-oxo-1H-[1,4]-N$^4$-trifluoroacetyl-azazino[3,4-a][2]benzazepine-4-carboxylic acid, diphenylmethyl ester (0.045 mmol) in methylene chloride (1 mL). Add trifluoroacetic acid (1 mL) and anisole (0.2 mL). Allow to stand for 3 hours under an argon atmosphere. Partition between methylene chloride and 1N hydrochloric acid. Separate the aqueous phase and freeze dry. Purify by High Pressure Liquid Chromatography to give the title compound.

EXAMPLE 12

[4S,[4α,7α(R*),12bβ]]-7-[(S-1-Carboxy-3-phenylpropyl)amino]-3,4,6,7,8,12b-hexahydro-9-nitro-6-oxo-1H-[1,4]-azazino[3,4-a][2]benzazepine-4-carboxylic acid Dissolve [4S-[4α,7α(R*),12bβ]]-7-[(S-1-carboxy-3--phenylpropyl)amino]-3,4,6,7,8,12b-hexahydro-9-nitro-6-oxo-1H-[1,4]-N$^4$-trifluoroacetyl-azazino[3,4-a][2]benzazepine-4-carboxylic acid (2.3 mmol) in tetrahydrofuran (10 mL) at 0° C. then treat with 1N lithium hydroxide (6.75 mL). Add ethanol(2–3 mL) and stir for 30 minutes at 0° C. Partition between ethyl acetate and water and separate the organic phase. Wash with water, dry (MgSO$_4$) and evaporate the solvent in vacuo to give the title compound.

The following compounds can be prepared by analogous procedures to those described above in Examples 1–12:

[4S-[4α,7α(R*),12bβ]]-7-[( S-1-Carboxy-3-phenylpropyl)amino]-3,4,6,7,8,12b-hexahydro-11-nitro-6-oxo-1H-[1,4]-N$^4$-trifluoroacetyl-azazino[3,4-a][2]benzazepine-4-carboxylic acid;

[4S-[4α,7α(R*),12bβ]]-7-[(S-1-Carboxy-3-phenylpropyl)amino]-3,4,6,7,8,12b-hexahydro-9-amino-6-oxo-1H-[1,4]-N$^4$-trifluoroacetyl-azazino[3,4-a][2]benzazepine-4-carboxylic acid, dihydrochloride;

[4S-[4α,7α(R*),12bβ]]-7-[(S-1-Carboxy-3-phenylpropyl)amino]-3,4,6,7,8,12b-hexahydro-11-amino-6-oxo-1H-[1,4]-N$^4$-trifluoroacetyl-azazino[3,4-a][2]benzazepine-4-carboxylic acid, dihydrochloride;

[4S-[4α,7α(R*),12bβ]]-7-[(S-1-Carboethoxy-3-phenylpropyl)amino]-3,4,6,7,8,12b-hexahydro-11-nitro-6-oxo-1H-[1,4]-N$^4$-trifluoroacetyl-azazino[3,4-a][2]benzazepine-4-carboxylic acid;

[4S-[4α,7α(R*),12bβ]]-7-[(S-1-Carboethoxy-3-phenylpropyl)amino]-3,4,6,7,8,12b-hexahydro-11-nitro-6-oxo-1H-[1,4]-N$^4$-trifluoroacetyl-azazino[3,4-a][2]benzazepine-4-carboxylic acid;

[4S-[4α,7α(R*),12bβ]]-7-[(S-1-Carboethoxy-3-phenylpropyl)amino]-3,4,6,7,8,12b-hexahydro-9-amino-6-oxo-1H-[1,4]-N$^4$-trifluoroacetyl-azazino[3,4-a][2]benzazepine-4-carboxylic acid, dihydrochloride;

[4S-[4α,7α(R*),12bβ]]-7-[(S-1-Carboethoxy-3-phenyl-propyl)amino]-3,4,6,7,8,12b-hexahydro-11-amino-6-oxo-1H-[1,4]-N⁴-trifluoroacetyl-azazino[3,4-a][2]benzazepine-4-carboxylic acid, dihydrochloride;

[4S-[4α,7α(R*),12bβ]]-7-[(S-1-Carboxy-3-phenyl-propyl)amino]-3,4,6,7,8,12b-hexahydro-11-nitro-6-oxo-1H-[1,4]-azazino[3,4-a][2]benzazepine-4-carboxylic acid;

[4S-[4α,7α(R*),12bβ]]-7-[(S-1-Carboxy-3-phenyl-propyl)amino]-3,4,6,7,8,12b-hexahydro-9-amino-6-oxo-1H-[1,4]-azazino[3,4-a][2]benzazepine-4-carboxylic acid, dihydrochloride;

[4S-[4α,7α(R*),12bβ]]-7-[(S-1-Carboxy-3-phenyl-propyl)amino]-3,4,6,7,8,12b-hexahydro-11-amino-6-oxo-1H-[1,4]-azazino[3,4-a][2]benzazepine-4-carboxylic acid, dihydrochloride;

[4S-[4α,7α(R*),12bβ]]-7-[( S-1-Carboethoxy-3-phenyl-propyl)amino]-3,4,6,7,8,12b-hexahydro-11-nitro-6-oxo-1H-[1,4]-azazino[3,4-a ][2]benzazepine-4-carboxylic acid;

[4S-[4α,7α(R*),12bβ]]-7-[(S-1-Carboethoxy-3-phenyl-propyl)amino]-3,4,6,7,8,12b-hexahydro-11-nitro-6-oxo-1H-[1,4]-azazino[3,4-a][2]benzazepine-4-carboxylic acid;

[4S-[4α,7α(R*),12bβ]]-7-[(S-1-Carboethoxy-3-phenyl-propyl)amino]-3,4,6,7,8,12b-hexahydro-9-amino-6-oxo-1H-[1,4]-azazino[3,4-a][2]benzazepine-4-carboxylic acid, dihydrochloride;

[4S-[4α,7α(R*),12bβ]]-7-[(S-1-Carboethoxy-3-phenyl-propyl)amino]-3,4,6,7,8,12b-hexahydro-11-amino-6-oxo-1H-[1,4]-azazino[3,4-a ][2]benzazepine-4-carboxylic acid, dihydrochloride;

[4S-[4α,7α(R*),12bβ]]-7-[( S-1-Carboxy-3-phenyl-propyl)amino]-3,4,6,7,8,12b-hexahydro-11-nitro-6-oxo-1H-[1,4]-thiazino[3,4-a][2]benzazepine-4-carboxylic acid;

[4S-[4α,7α(R*),12bβ]]-7-[(S-1-Carboxy-3-phenyl-propyl)amino ]-3,4,6,7,8,12b-hexahydro-9-amino-6-oxo-1H-[1,4]-thiazino[3,4-a][2]benzazepine-4-carboxylic acid, dihydrochloride;

[4S-[4α,7α(R*),12bβ]]-7-[(S-1-Carboxy-3-phenyl-propyl)amino]-3,4,6,7,8,12b-hexahydro-11-amino-6-oxo-1H-[1,4]-thiazino[3,4-a][2]benzazepine-4-carboxylic acid, dihydrochloride;

[4S-[4α,7α(R*),12bβ]]-7-[(S-1-Carboethoxy-3-phenyl-propyl)amino]-3,4,6,7,8,12b-hexahydro-11-nitro-6-oxo-1H-[1,4]-thiazino[3,4-a][2]benzazepine-4-carboxylic acid;

4S-[4α,7α(R*),12bβ]]-7-[(S-1-Carboethoxy-3-phenyl-propyl)amino]-3,4,6,7,8,12b-hexahydro-11-nitro-6-oxo-1H-[1,4]-thiazino[3,4-a][2]benzazepine-4-carboxylic acid;

[4S-[4α,7α(R*),12bβ]]-7-[(S-1-Carboethoxy-3-phenyl-propyl)amino]-3,4,6,7,8,12b-hexahydro-9-amino-6-oxo-1H-[1,4]-thiazino[3,4-a][2]benzazepine-4-carboxylic acid, dihydrochloride;

[4S-[4α,7α(R*),12bβ]]-7-[(S-1-Carboethoxy-3-phenyl-propyl)amino]-3,4,6,7,8,12b-hexahydro-11-amino-6-oxo-1H-[1,4]-thiazino[3,4-a][2]benzazepine-4-carboxylic acid, dihydrochloride;

[4S-[4α,7α(R*),12bβ]]-7-[(S-1-Carboxy-3-phenyl-propyl)amino]-3,4,6,7,8,12b-hexahydro-11-nitro-6-oxo-1H-[1,4]-oxazino[3,4-a][2]benzazepine-4-carboxylic acid;

[4S-[4α,7α(R*),12bβ]]-7-[(S-1-Carboxy-3-phenyl-propyl)amino]-3,4,6,7,8,12b-hexahydro-9-amino-6-oxo-1H-[1,4]-oxazino[3,4-a][2]benzazepine-4-carboxylic acid, dihydrochloride;

[4S-[4α,7α(R*),12bβ]]-7-[(S-1-Carboxy-3-phenyl-propyl)amino]-3,4,6,7,8,12b-hexahydro-11-amino-6-oxo-1H-[1,4]-oxazino[3,4-a][2]benzazepine-4-carboxylic acid, dihydrochloride;

[4S-[4α,7α(R*),12bβ]]-7-[(S-1-Carboethoxy-3-phenyl-propyl)amino]3,4,6,7,8,12b-hexahydro-11-nitro-6-oxo-1H-[1,4]-oxazino[3,4-a][2]benzazepine-4-carboxylic acid;

[4S-[4α,7α(R*),12bβ]]-7-[(S-1-Carboethoxy-3-phenyl-propyl)amino]-3,4,6,7,8,12b-hexahydro-11-nitro-6-oxo-1H-[1,4]-oxazino[3,4-a][2]benzazepine-4-carboxylic acid;

[4S-[4α,7α(R*),12bβ]]-7-[(S-1-Carboethoxy-3-phenyl-propyl)amino]-3,4,6,7,8,12b-hexahydro-9-amino-6-oxo-1H-[1,4]-oxazino[3,4-a][2]benzazepine-4-carboxylic acid, dihydrochloride;

[4S-[4α,7α(R*),12bβ]]-7-[(S-1-Carboethoxy-3-phenyl-propyl)amino]-3,4,6,7,8,12b-hexahydro-11-amino-6-oxo-1H-[1,4]-oxazino[3,4-a ][2]benzazepine-4-carboxylic acid, dihydrochloride.

In a further embodiment, the present invention provides a method of inhibiting ACE in a patient in need thereof comprising administering to said patient an effective ACE inhibitory amount of a compound of formula (1).

As used herein, the term "patient" refers to warm-blooded animals or mammals, including mice, rats and humans. A patient is in need of treatment to inhibit ACE when it would be beneficial to the patient to reduce the physiological effect of circulating angiotensin II. For example, a patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyper-aldosteronemic effects caused thereby.

An effective ACE inhibitory amount of a compound of formula (1) is that amount which is effective in inhibiting ACE in a patient in need thereof which results, for example, in a hypotensive effect.

An effective ACE inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective ACE inhibitory amount of a compound of formula (1) will generally vary from about 0.01 milligram per kilogram of body weight per day (mg/kg/day) to about 20 mg/kg/day. A daily dose of from about 0.1 mg/kg to about 10 mg/kg is preferred.

In effecting treatment of a patient, compounds of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (1) can be administered in the form of pharmaceutical compositions or medicaments which are made by combining the compounds of formula (1) with pharmaceutically acceptable carriers or excipients, the proportion and nature of which are determined by the chosen route of administration, and standard pharmaceutical practice.

In another embodiment, the present invention provides compositions comprising a compound of formula (1) in admixture or otherwise in association with one or more inert carriers. These compositions are useful, for example, as assay standards, as convenient means of making bulk shipments, or as pharmaceutical compositions. An assayable amount of a compound of formula (1) is an amount which is readily measurable by standard assay procedures and techniques as are well known and appreciated by those skilled in the art. Assayable amounts of a compound of formula (1) will generally vary from about 0.001% to about 75% of the composition by weight. Inert carriers can be any material which does not degrade or otherwise covalently react with a compound of formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (1) in admixture or otherwise in association with one or more pharmaceutically acceptable carriers or excipients.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (1) may be incorporated with excipients and used in the form of tablets, troches, capsules, elixirs, suspensions, syrups, wafers, chewing gums and the like. These preparations should contain at least 4% of the compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (1) in their end-use application.

The compounds of formula (1) wherein X is amino and Y is hydrogen are generally preferred.

It is, of course, understood that the compounds of formula (1) exist in particular isomeric configurations including structural as well as stereo isomers. It is further understood that the present invention encompasses those compounds in the particular isomeric configurations depicted by the structure of formula (1) which utilizes standard techniques and conventions for drawing isomeric structures.

The following specific compounds of formula (1) are particularly preferred in the end-use application of the compounds of the present invention:

[4S-[4α,7α(R*),12bβ]]-7-[(S-1-Carboxy-3-phenylpropyl)amino]-1,2,3,4,6,7,8,12b-octahydro-9-nitro-6-oxopyrido[2,1-a][2]benzazepine-4-carboxylic acid;

[4S-[4α,7α(R*),12bβ]]-9-Amino-7-[(S-1-carboxy-3-phenylpropyl)amino]-1,2,3,4,6,7,8,12b-octahydro-6oxopyrido[2,1-a][2]benzazepine-4-carboxylic acid, dihydrochloride;

[4S-[4α,7α(R*),12bβ]]-7-[(S-1-Carboxy-3-phenylpropyl)amino]-1,2,3,4,6,7,8,12b-octahydro-11-nitro-6-oxopyrido[2,1-a][2]benzazepine-4-carboxylic acid;

[4S-[4α,7α(R*),12bβ]]-11-Amino-7-[(S-1-carboxy-3-phenylpropyl)amino]-1,2,3,4,6,7,8,12b-octahydro-6oxopyrido[2,1-a ][2]benzazepine-4-carboxylic acid, dihydrochloride;

[4S-[4α,7α(R*),12bβ]]-7-[(S-1-Carbethoxy-3-phenylpropyl)amino]-1,2,3,4,6,7,8,12b-octahydro-9-nitro-6oxopyrido[2,1-a][2]benzazepine-4-carboxylic acid;

[4S-[4α,7α(R*),12bβ]]-9-Amino-7-[(1-carbethoxy-3-phenylpropyl)amino]-1,2,3,4,6,7,8,12b-octahydro-6-oxopyrido[2,1-a][2]benzazepine-4-carboxylic acid dihydrochloride;

[4S-[4α,7α(R*),12bβ]]-7-[(S-1-Carbethoxy-3-phenylpropyl)amino]-1,2,3,4,6,7,8,12b-octahydro-11-nitro-6oxopyrido[2,1-a][2]benzazepine-4-carboxylic acid;

[4S-[4α,7α(R*),12bβ]]-11-Amino-7-[(S-1-carbethoxy-3-phenylpropyl)amino]-1,2,3,4,6,7,8,12b-octahydro-6oxopyrido[2,1-a][2]benzazepine-4-carboxylic acid, dihydrochloride;

The utility of the compounds of formula (1) may be demonstrated by monitoring the inhibition of ACE in vitro using the spectrophotometric substrate described by Holmquist et al. [*Anal. Biochem.* 95, 540–548 (1979)] and the buffer system described by Ryan [*Methods of Enzymatic Analysis*, 3rd ed., H. U. Bergmeyer, editor; vol. V, Verlag Chemie, Weinheim, 1983, pp. 20–34].

The amino or nitro substituted compounds of the present invention possess an unexpectedly prolonged duration of activity as compared to other ACE inhibitors similar in structure.

What is claimed is:

1. A compound of the formula

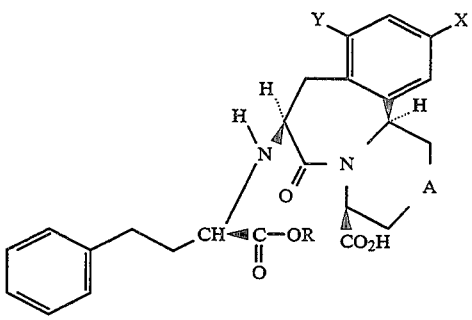

wherein
A is sulfur;
R is hydrogen or a $C_1$–$C_4$ alkyl; and
X and Y are each independently hydrogen, nitro or amino, with the proviso that one of X and Y is hydrogen and one of X and Y is other than hydrogen; and pharmaceutically acceptable salts thereof.

2. A compound of claim 1 wherein Y is nitro and X is hydrogen.
3. A compound of claim 1 wherein Y is amino and X is hydrogen.
4. A compound of claim 1 wherein X is nitro and Y is hydrogen.
5. A compound of claim 1 wherein X is amino and Y is hydrogen.
6. A pharmaceutical composition comprising an effective ACE inhibitory amount of a compound of claim 1 in admixture or otherwise in association with one or more pharmaceutically acceptable carriers or excipients.
7. A method of inhibiting ACE in a patient in need thereof comprising administering to said patient an effective ACE inhibitory amount of a compound of claim 1.
8. A compound of claim 1 wherein A is sulfur.
9. A method of claim 7 wherein the patient is suffering from hypertension.
10. A method of claim 7 wherein the patient is suffering from chronic congestive heart failure.

* * * * *

UNITED STATES PATENT AND TRADEMARK OFFICE
CERTIFICATE OF CORRECTION

PATENT NO. : 5,389,628
DATED : February 14, 1995
INVENTOR(S) : Gary A. Flynn and Douglas W. Beight It is certified that error appears in the above-indentified patent and that said Letters Patent is hereby corrected as shown below:

Column 5, Line 57, patent reads: " compound s " and should read -- compounds --.

Column 5, Line 68 patent reads: " diphenylmetheyl " and should read -- diphenylmethyl --.

Column 6, Line 64, patent reads: " an appreciated " and should read -- and appreciated --.

Column 9, Line 14, patent reads: " an appreciated " and should read -- and appreciated --.

Column 14, Line 6, patent reads: " -Dihydro1,3-dioxo " and should read -- -Dihydro-1,3-dioxo --.

Column 15, Line 42, patent reads: " 5,82; " and should read -- 5.82; --.

Column 16, Line 18, patent reads: " dissolve " and should read -- Dissolve --.

Column 16, Line 29, patent reads: " -nitro6-oxopyrido " and should read -- -nitro-6-oxopyrido --.

Column 16, Line 43, patent reads: " 00% " and should read -- 100% --.

Column 16, Line 44, patent reads: " Step b: " and should read -- Step d: --.

Column 16, Line 46, patent reads: " 6,6,8 " and should read -- 6,7,8 --.

Column 16, Line 63, patent reads: " [bS- " and should read -- [4S- --.

Column 17, Line 1, patent reads: " 812b- " and should read -- 8,12b- --.

Column 17, Line 18, patent reads: " [2,1-] " and should read -- [2,1-a] --.

Column 17, Line 27, patent reads: " between in 1N " and should read -- between 1N --.

UNITED STATES PATENT AND TRADEMARK OFFICE
CERTIFICATE OF CORRECTION

PATENT NO. : 5,389,628

DATED : February 14, 1995

INVENTOR(S) : Gary A. Flynn and Douglas W. Beight

It is certified that error appears in the above-indentified patent and that said Letters Patent is hereby corrected as shown below:

Column 17, Line 39, patent reads: " [2,1-] " and should read -- [2,1-a] --.

Column 18, Line 5, patent reads: " [2,1-[ " and should read -- [2,1-a] --.

Column 18, Line 8, patent reads: " 6,7,87 " and should read -- 6,7,8 --.

Column 18, Line 49, patent reads: " 6oxopyrido " and should read -- 6-oxopyrido --.

Column 19, Line 1, patent reads: " 6oxopyrido " and should read -- 6-oxopyrido --.

Column 19, Line 2, patent reads: " 38 5 mmol) " and should read -- 385mmol) --.

Column 19, Line 15, patent reads: " [3,4a] " and should read -- [3,4-a] --.

Column 19, Line 57, patent reads: " dioxo2H- " and should read -- dioxo-2H- --.

Column 20, Line 48, patent reads: " hexaahydro " and should read -- hexahydro --.

Column 21, Line 32, patent reads: " 1H-[4] " and should read -- 1H-[1,4] --.

Column 23, Line 31, patent reads: " [3,4-] " and should read -- [3,4-a] --.

Column 23, Line 41, patent reads: " 1 hours " and should read -- 1 hour --.

Column 24, Line 25 & 26, patent reads: " -3-phenyl propyl]-(S)-3-[trifluoroacetyl-2propenyl) " and should read -- -3-phenylpropyl]-(S)-3-[trifluoroacetyl-2-propenyl) --.

Column 24, Line 44, patent reads: " )amino-propionic acid, " and should read -- )amino]-2-amino-propionic acid, --.

UNITED STATES PATENT AND TRADEMARK OFFICE
CERTIFICATE OF CORRECTION

PATENT NO. : 5,389,628
DATED : February 14, 1995
INVENTOR(S) : Gary A. Flynn and Douglas W. Beight It is certified that error appears in the above-indentified patent and that said Letters Patent is hereby corrected as shown below:

Column 25, Line 48, patent reads: " acids. " and should read -- acid, --.

Column 26, Line 14, patent reads: " 07- " and should read -- -7- --.

Column 30, Line 57, patent reads: " 6oxopyrido " and should read -- 6-oxopyrido --.

Column 30, Line 64, patent reads: " 6oxopyrido " and should read -- 6-oxopyrido --.

Column 30, Line 67, patent reads: " 6oxopyrido " and should read -- 6-oxopyrido --.

Column 31, Line 11, patent reads: " 6oxopyrido " and should read -- 6-oxopyrido --.

Column 31, Line 19, patent reads: " 6oxopyrido " and should read -- 6-oxopyrido --.

Signed and Sealed this

Fifth Day of March, 1996

Attest:

BRUCE LEHMAN

Attesting Officer

Commissioner of Patents and Trademarks